(12) United States Patent
First et al.

(10) Patent No.: US 10,781,437 B2
(45) Date of Patent: Sep. 22, 2020

(54) D-STEREOSPECIFIC AMINOACYL-TRNA SYNTHETASE AND METHOD OF PRODUCING D-STEREOSPECIFIC AMINOACYL-TRNA SYNTHETASE

(71) Applicant: Board of Supervisors of Louisiana State University and Agricultural and Mechanical College, Baton Rouge, LA (US)

(72) Inventors: Eric Allen First, Shreveport, LA (US); Charles Joseph Richardson, Shreveport, LA (US)

(73) Assignee: BOARD OF SUPERVISORS OF LOUISIANA STATE UNIVERSITY, Baton Rouge, LA (US)

( * ) Notice: Subject to any disclaimer, the term of this patent is extended or adjusted under 35 U.S.C. 154(b) by 0 days.

(21) Appl. No.: 15/274,372

(22) Filed: Sep. 23, 2016

(65) Prior Publication Data

US 2017/0088829 A1    Mar. 30, 2017

Related U.S. Application Data

(60) Provisional application No. 62/222,911, filed on Sep. 24, 2015.

(51) Int. Cl.
| | | |
|---|---|---|
| *C12N 9/00* | (2006.01) | |
| *C12N 15/00* | (2006.01) | |
| *C12P 21/00* | (2006.01) | |

(52) U.S. Cl.
CPC .............. *C12N 9/93* (2013.01); *C12N 15/00* (2013.01); *C12P 21/00* (2013.01); *C12Y 601/01001* (2013.01)

(58) Field of Classification Search
None
See application file for complete search history.

(56) References Cited

PUBLICATIONS

Branden. Introduction to Protein Structure, Garland Publishing Inc., New York, p. 247, 1991).*
Schaefer Predict impact of single amino acid change upon protein structure. BMC Genomics 2012, 13(Suppl 4):S4.*
Leiman. Identification and characterization of mutations conferring resistance to D-amino acids in Bacillus subtilis. J Bacteriol. May 2015;197(9):1632-9. Epub Mar. 2, 2015.*
Richardson Altering the Enantioselectivity of Tyrosyl-tRNA Synthetase by Insertion of a Stereospecific Editing Domain. Biochemistry. Mar. 15, 2016;55(10):1541-53. Epub Mar. 2, 2016.*
Oki. Transplantation of a tyrosine editing domain into a tyrosyl-tRNA synthetase variant enhances its specificity for a tyrosine analog. Proc Natl Acad Sci U S A. Sep. 9, 2008;105(36):13298-303. Epub Sep. 2, 2008.*
Sheoran. Activation of D-Tyrosine by Bacillus stearothermophilus Tyrosyl-tRNA Synthetase. The Journal of Biological Chemistry. vol. 283, No. 19, pp. 12960-12970, May 9, 2008.*
Kawarabayasi. O73984. UniProtKB Database. May 2013.*
Sasaki. Structural and mutational studies of the amino acid-editing domain from archaeal eukaryal phenylalanyl-tRNA synthetase. PNAS. vol. 103, No. 40, pp. 14744-14749, Oct. 3, 2006.*

\* cited by examiner

*Primary Examiner* — Yong D Pak
(74) *Attorney, Agent, or Firm* — Davis & Bujold PLLC; Charles Holoubek; Michael Bujold

(57) ABSTRACT

A method for one of altering and enhancing the stereospecificity of an enzyme comprising introducing a stereospecific editing domain into the enzyme.

13 Claims, 17 Drawing Sheets

Specification includes a Sequence Listing.

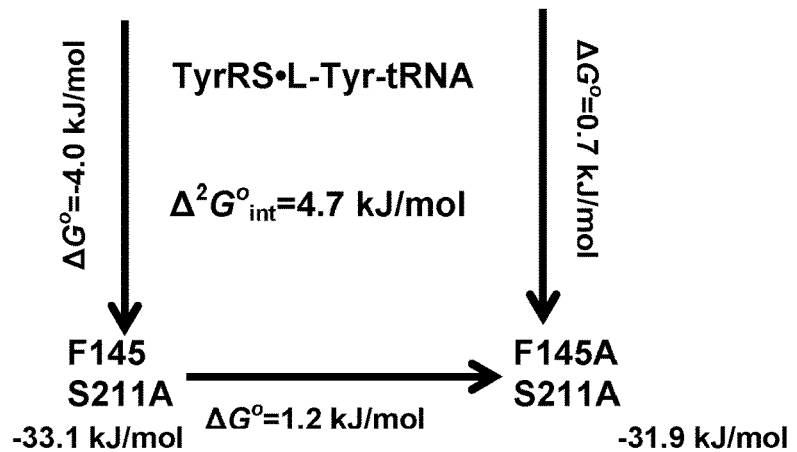
Fig. 6A
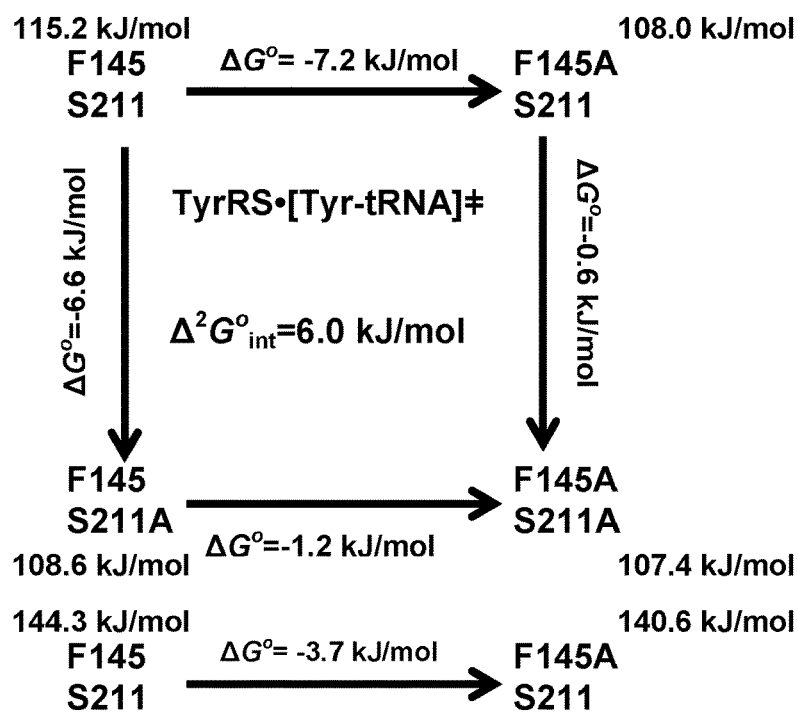
Fig. 6B
Fig. 6C

Fig. 11G
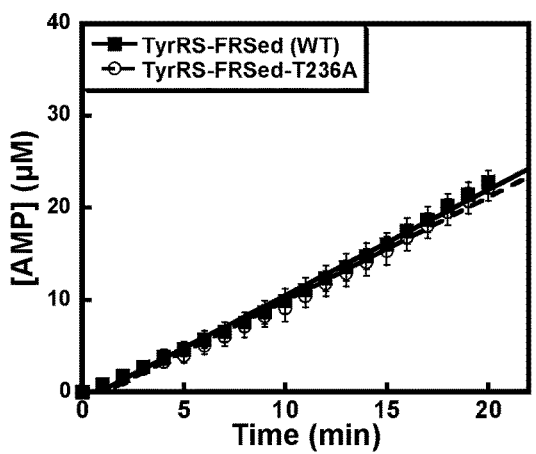
Fig. 11H
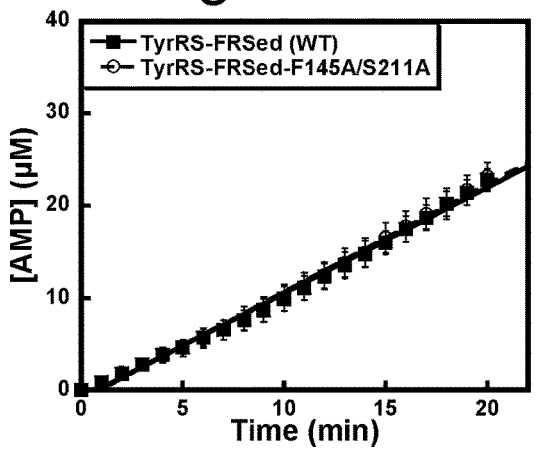
Fig. 11I
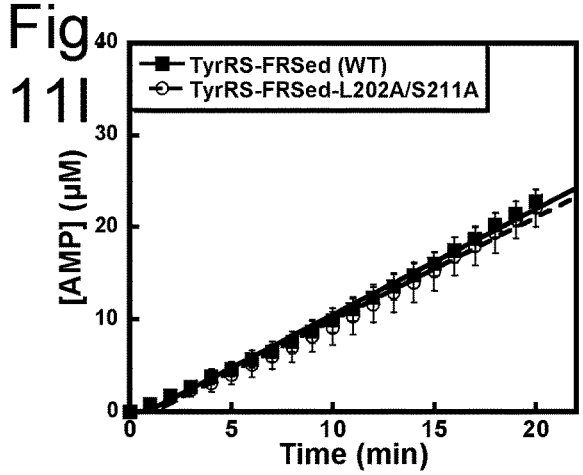
Fig. 11J
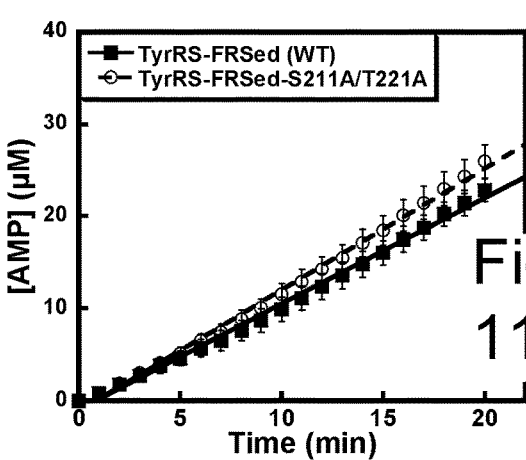
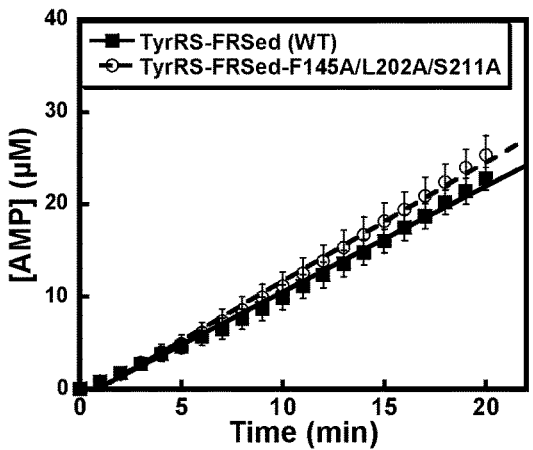
Fig. 11K
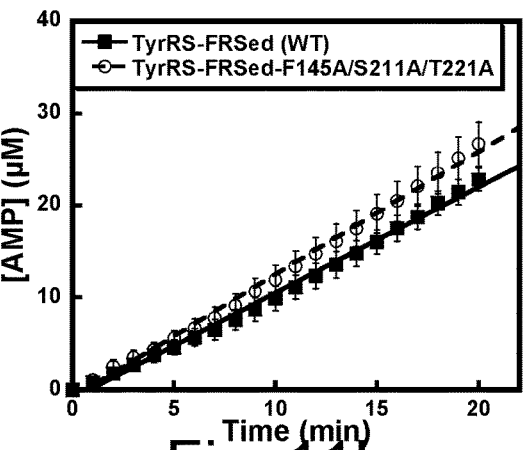
Fig. 11L

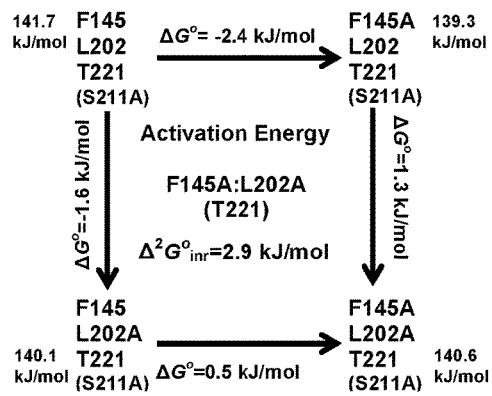
Fig. 14A
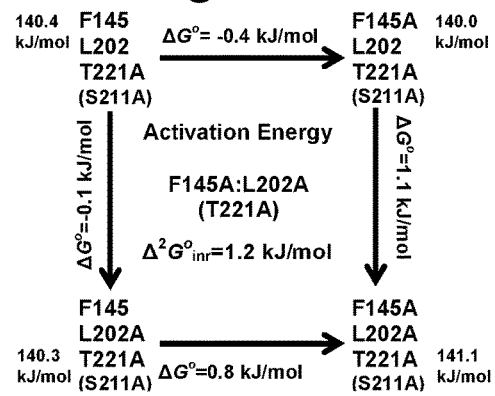
Fig. 14D
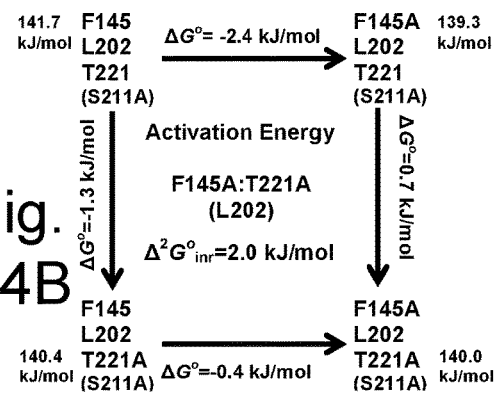
Fig. 14B
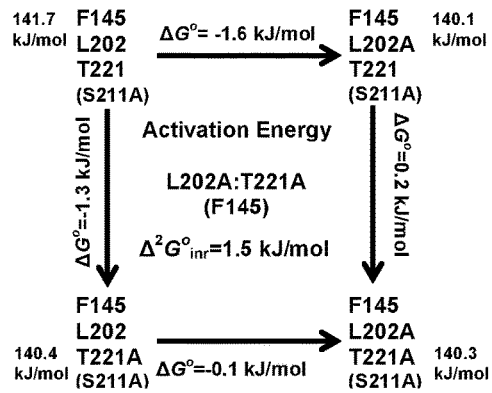
Fig. 14C
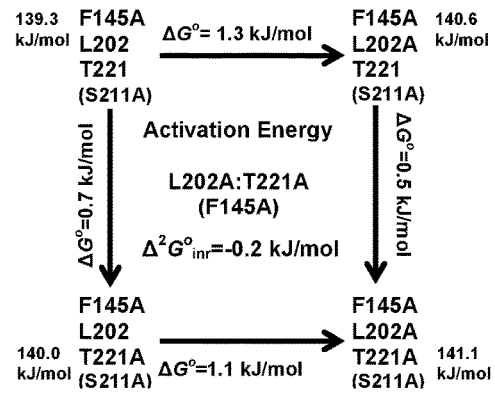
Fig. 14E
Fig. 14F

SEQUENCE LISTING

<160> NUMBER OF SEQ ID NOS: 2

<210> SEQ ID NO 1
<211> LENGTH: 556
<212> TYPE: PRT
<213> ORGANISM: Pyrococcus horikoshii -continued

```
<400> SEQUENCE: 1

Met Pro Lys Phe Asp Val Ser Lys Ser Asp Leu Glu Arg Leu Ile Gly
1               5                   10                  15

Arg Ser Phe Ser Ile Glu Glu Trp Glu Asp Leu Val Leu Tyr Ala Lys
                20                  25                  30

Cys Glu Leu Asp Asp Val Trp Glu Asn Gly Lys Val Tyr Phe Lys
            35                  40                  45

Leu Asp Ser Lys Asp Thr Asn Arg Pro Asp Leu Trp Ser Ala Glu Gly
        50                  55                  60

Val Ala Arg Gln Ile Lys Trp Ala Leu Gly Ile Glu Lys Gly Leu Pro
65                  70                  75                  80

Lys Tyr Glu Val Lys Lys Ser Asn Val Thr Val Tyr Val Asp Glu Lys
                85                  90                  95

Leu Lys Asp Ile Arg Pro Tyr Gly Val Tyr Ala Ile Val Glu Gly Leu
            100                 105                 110

Arg Leu Asp Glu Asp Ser Leu Ser Gln Met Ile Gln Leu Gln Glu Lys
        115                 120                 125

Ile Ala Leu Thr Phe Gly Arg Arg Arg Glu Val Ala Ile Gly Ile
    130                 135                 140

Phe Asp Phe Asp Lys Ile Lys Pro Pro Ile Tyr Tyr Lys Ala Ala Glu
145                 150                 155                 160

Lys Thr Glu Lys Phe Ala Pro Leu Gly Tyr Lys Glu Glu Met Thr Leu
                165                 170                 175

Glu Glu Ile Leu Glu Lys His Glu Lys Gly Arg Glu Tyr Gly His Leu
            180                 185                 190

Ile Lys Asp Lys Gln Phe Tyr Pro Leu Leu Ile Asp Ser Glu Gly Asn
        195                 200                 205

Val Leu Ser Met Pro Pro Ile Ile Asn Ser Glu Phe Thr Gly Arg Val
210                 215                 220

Thr Thr Asp Thr Lys Asn Val Phe Ile Asp Val Thr Gly Trp Lys Leu
225                 230                 235                 240

Glu Lys Val Met Leu Ala Leu Asn Val Met Val Thr Ala Leu Ala Glu
                245                 250                 255

Arg Gly Gly Lys Ile Arg Ser Val Arg Val Val Tyr Lys Asp Phe Glu
            260                 265                 270

Ile Glu Thr Pro Asp Leu Thr Pro Lys Glu Phe Glu Val Glu Leu Asp
        275                 280                 285

Tyr Ile Arg Lys Leu Ser Gly Leu Glu Leu Asn Asp Gly Glu Ile Lys
290                 295                 300

Glu Leu Leu Glu Lys Met Met Tyr Glu Val Glu Ile Ser Arg Gly Arg
305                 310                 315                 320

Ala Lys Leu Lys Tyr Pro Ala Phe Arg Asp Ile Met His Ala Arg
                325                 330                 335

Asp Ile Leu Glu Asp Val Leu Ile Ala Tyr Gly Tyr Asn Asn Ile Glu
            340                 345                 350

Pro Glu Glu Pro Lys Leu Ala Val Gln Gly Arg Gly Asp Pro Phe Lys
        355                 360                 365

Asp Phe Glu Asp Ala Ile Arg Asp Leu Met Val Gly Phe Gly Leu Gln
370                 375                 380

Glu Val Met Thr Phe Asn Leu Thr Asn Lys Glu Val Gln Phe Lys Lys
385                 390                 395                 400

Met Asn Ile Pro Glu Glu Glu Ile Val Glu Ile Ala Asn Pro Ile Ser
                405                 410                 415
```

```
Gln Arg Trp Ser Ala Leu Arg Lys Trp Ile Leu Pro Ser Leu Met Glu
                420                 425                 430

Phe Leu Ser Asn Asn Thr His Glu Glu Tyr Pro Gln Arg Ile Phe Glu
            435                 440                 445

Val Gly Leu Ala Thr Leu Ile Asp Glu Ser Arg Glu Thr Lys Thr Val
        450                 455                 460

Ser Glu Pro Lys Leu Ala Val Ala Leu Ala Gly Thr Gly Tyr Thr Phe
465                 470                 475                 480

Thr Asn Ala Lys Glu Ile Leu Asp Ala Leu Met Arg His Leu Gly Phe
                485                 490                 495

Glu Tyr Glu Ile Glu Glu Val Glu His Gly Ser Phe Ile Pro Gly Arg
            500                 505                 510

Ala Gly Lys Ile Ile Val Asn Gly Arg Asp Ile Gly Ile Ile Gly Glu
        515                 520                 525

Val His Pro Gln Val Leu Glu Asn Trp Asn Ile Glu Val Pro Val Val
530                 535                 540

Ala Phe Glu Ile Phe Leu Arg Pro Leu Tyr Arg His
545                 550                 555

<210> SEQ ID NO 2
<211> LENGTH: 419
<212> TYPE: PRT
<213> ORGANISM: Geobacillus stearothermophilus

<400> SEQUENCE: 2

Met Asp Leu Leu Ala Glu Leu Gln Trp Arg Gly Leu Val Asn Gln Thr
1               5                   10                  15

Thr Asp Glu Asp Gly Leu Arg Lys Leu Leu Asn Glu Glu Arg Val Thr
                20                  25                  30

Leu Tyr Cys Gly Phe Asp Pro Thr Ala Asp Ser Leu His Ile Gly Asn
            35                  40                  45

Leu Ala Ala Ile Leu Thr Leu Arg Arg Phe Gln Gln Ala Gly His Arg
        50                  55                  60

Pro Ile Ala Leu Val Gly Gly Ala Thr Gly Leu Ile Gly Asp Pro Ser
65                  70                  75                  80

Gly Lys Lys Ser Glu Arg Thr Leu Asn Ala Lys Glu Thr Val Glu Ala
                85                  90                  95

Trp Ser Ala Arg Ile Lys Glu Gln Leu Ser Arg Phe Leu Asp Phe Glu
            100                 105                 110

Ala Lys Asp Asn Ala Ala Glu Ile Lys Asn Asn Tyr Asp Trp Ile Gly
        115                 120                 125

Pro Leu Asp Val Ile Ser Phe Leu Arg Asp Val Gly Lys His Phe Ser
130                 135                 140

Val Asn Tyr Met Leu Ala Lys Glu Ser Val Gln Ser Arg Ile Glu Thr
145                 150                 155                 160

Gly Ile Ser Phe Thr Glu Phe Tyr Met Met Leu Gln Ala Tyr Asp
            165                 170                 175

Phe Leu Arg Leu Tyr Glu Thr Glu Gly Cys Arg Leu Gln Ile Gly Gly
        180                 185                 190

Ser Asp Gln Trp Gly Asn Ile Thr Ala Gly Leu Glu Leu Ile Arg Lys
            195                 200                 205

Thr Lys Gly Glu Ala Lys Ala Phe Gly Leu Thr Ile Pro Leu Val Thr
        210                 215                 220

Lys Ala Asp Gly Thr Lys Phe Gly Lys Thr Glu Ser Gly Thr Ile Trp
```

```
                225                 230                 235                 240

Leu Asp Pro Glu Lys Thr Ser Pro Tyr Glu Phe Tyr Gln Phe Trp Ile
                    245                 250                 255

Asn Thr Asp Asp Arg Asp Val Ile Arg Tyr Leu Lys Tyr Phe Thr Phe
                    260                 265                 270

Leu Ser Lys Glu Glu Ile Glu Ala Leu Glu Gln Glu Leu Arg Glu Ala
            275                 280                 285

Pro Glu Lys Arg Ala Ala Gln Lys Ala Leu Ala Glu Glu Val Thr Lys
            290                 295                 300

Leu Val His Gly Glu Glu Ala Leu Arg Gln Ala Ile Arg Ile Ser Glu
305                 310                 315                 320

Ala Leu Phe Ser Gly Asp Ile Ala Asn Leu Thr Ala Ala Glu Ile Glu
                325                 330                 335

Gln Gly Phe Lys Asn Val Pro Ser Phe Val His Glu Gly Gly Asp Val
                340                 345                 350

Pro Leu Val Glu Leu Leu Val Ala Ala Gly Ile Ser Pro Ser Lys Arg
                355                 360                 365

Gln Ala Arg Glu Asp Ile Gln Asn Gly Ala Ile Tyr Val Asn Gly Glu
            370                 375                 380

Arg Leu Gln Asp Val Gly Ala Ile Leu Thr Ala Glu His Arg Leu Glu
385                 390                 395                 400

Gly Arg Phe Thr Val Ile Arg Arg Gly Lys Lys Lys Tyr Tyr Leu Ile
                405                 410                 415

Arg Tyr Ala
```

US 10,781,437 B2

D-STEREOSPECIFIC AMINOACYL-TRNA SYNTHETASE AND METHOD OF PRODUCING D-STEREOSPECIFIC AMINOACYL-TRNA SYNTHETASE

CROSS REFERENCE TO RELATED APPLICATIONS/PRIORITY

The present invention claims priority to U.S. Provisional Patent Application No. 62/222,911 filed Sep. 24, 2015, which, including its Appendix Manuscript, is incorporated by reference in its entirety into the present disclosure as if fully restated herein. To the extent that there is any conflict between the incorporated material and the present disclosure, the present disclosure will control.

FIELD OF INVENTION

This invention relates generally to D-stereospecific enzymes and producing proteins with D-stereospecific amino acids, and specifically to D-stereospecific aminoacyl-tRNA synthetase and a method of producing D-stereospecific aminoacyl-tRNA synthetase.

BACKGROUND

Messenger RNA translation is stereospecific, with only L-amino acids being incorporated into the nascent polypeptide chain. Exclusion of D-amino acids from protein synthesis is due to the stereospecific selection of L-amino acids at three steps during translation. First, the aminoacyl-tRNA synthetases are highly selective, with only a few aminoacyl-tRNA synthetases able to aminoacylate tRNA with the D-stereoisomer of their cognate amino acid (albeit at a significantly reduced rate). Second, EF-Tu (in bacteria) and presumably EF-1α (in eukaryotes and archaea) are unable to bind and transport D-aminoacyl-tRNAs to the ribosome, preventing their use in protein synthesis. Third, the ribosome itself strongly favors L-aminoacyl-tRNAs with both the peptidyl-transferase center and exit tunnel entrance proposed as being responsible for the stereospecificity of the ribosome. Although mutations have been identified in the peptidyl-transferase center that partially ameliorates the ribosome's inability to use D-aminoacyl-tRNAs, altering the stereoselectivity of aminoacyl-tRNA synthetases and EF-Tu (or EF-1α) remains a challenge in current practice.

Cell-free in vitro translation systems have demonstrated that D-amino acids can be incorporated into proteins, indicating that the *E. coli* translational system (i.e. aminoacyl-tRNA synthetases, EF-Tu, and the ribosome) can recognize and use D-amino acids and D-aminoacyl-tRNAs, albeit at much lower efficiencies than for L-amino acids and L-aminoacyl-tRNAs. For example, Dedkova et al. report efficiencies of 3-5% for the incorporation of D-amino acids into dihydrofolate reductase using *E. coli* extracts (the efficiencies of incorporation are relative to those of their L-amino acid counterparts). Fujino et al. have reported efficiencies of 40% or more for the incorporation of selected D-amino acids into short peptides using a recombinant in vitro translation system, providing further evidence that incorporating D-amino acids into proteins is feasible in vitro.

Although there has been some success incorporating D-amino acids into proteins in vitro (particularly for short peptides), in current practice, incorporating D-amino acids into recombinant proteins produced in *E. coli* requires a significant increase in the efficiency with which the translational machinery can use D-amino acids and D-aminoacyl-tRNAs. The invention described herein improves the efficiency of incorporating D-amino acids during protein synthesis. In doing so, the inventors have provided a method for the efficient synthesis of D-aminoacyl-tRNAs that can be used with in vitro translation systems and have opened the door to additional approaches (including, but not limited to, genetic selection methods) that can be used to further improve the efficiency of D-amino acid incorporation during the synthesis of recombinant proteins by *E. coli* and other organisms.

SUMMARY OF THE INVENTION

Wherefore, it is an object of the present invention to overcome the above mentioned shortcomings and drawbacks associated with the prior art As a first step towards overcoming the above roadblocks to incorporating D-amino acids into proteins, the inventors engineered tyrosyl-tRNA synthetase variants with altered stereospecificity. Specifically, the inventors inserted the editing domain from *Pyrococcus horikoshii* phenylalanyl-tRNA synthetase into the connective polypeptide 1 (CP1) domain of *Geobacillus stearothermophilus* tyrosyl-tRNA synthetase (Richardson and First APPENDIX manuscript). The resulting variant is designated TyrRS-FRSed. Insertion of the phenylalanyl-tRNA synthetase editing domain affects the stereospecificity of tyrosyl-tRNA synthetase in two ways. First, the editing domain hydrolyzes L-Tyr-tRNA but not D-Tyr-tRNA, specifically removing the unwanted L-Tyr-tRNA product. Second, it slows down the rate at which the synthetic site in tyrosyl-tRNA synthetase catalyzes the aminoacylation of tRNA. Slowing down the rate at which L-Tyr-tRNA is produced increases the ability of the editing domain to compete with the synthetic site, resulting in an increase in the fraction of L-Tyr-tRNA that is hydrolyzed. Together, these two effects resulted in a two-fold increase in the fraction of tRNA that is aminoacylated by D-tyrosine.

One of the lessons learned from inserting the editing domain into tyrosyl-tRNA synthetase is that there is a competition between the production of L-Tyr-tRNA by the synthetic site and its hydrolysis by the editing site. Normally, the non-cognate aminoacyl-tRNA is synthesized at low levels, allowing the aminoacyl-tRNA synthetase editing domain to keep up with non-cognate aminoacyl-tRNA synthesis. In the case of the engineered TyrRS-FRSed variant, however, L-Tyr-tRNA is the primary (albeit unwanted) product. As a result, shifting the balance towards D-Tyr-tRNA formation requires introducing mutations into TyrRS-FRSed that either decrease the synthesis of L-Tyr-tRNA or increase the activity of the editing site. Previously, and apparently tangentially, Yokoyama and colleagues identified six mutations in the phenylalanyl-tRNA synthetase editing domain that increase the phenylalanyl-tRNA synthetase editing activity: F145A, L202A, L210A, S211A, T221A, and T236A (collectively described herein as the Yokoyama mutations). The inventors were curious as to whether incorporating one or more of the phenylalanyl-tRNA synthetase editing domain Yokoyama mutations into TyrRS-FRSed were sufficient to shift the balance in favor of L-Tyr-AMP hydrolysis, the six mutations were introduced into the TyrRS-FRSed variant both individually and as multiple mutations. To monitor the effect that the Yokoyama mutations had on the activity of the phenylalanyl-tRNA synthetase editing domain, the inventors developed a continuous spectrophotometric editing assay that was amenable to a 96-well plate format. Using this assay, the inventors were able to determine both the effect that each individual mutation had on editing activity, and also the role that coupling between these amino acids played in editing.

Much to the surprise of the inventors, optimum editing activity was obtained when two residues were mutated, with editing activity decreasing when three or more mutations are introduced. One double mutant in particular, F145A/S211A, was able to switch the stereospecificity of the TyrRS-FRSed variant when L- and D-tyrosine were present at equimolar concentrations, making the particular TyrRS-FRSed variant a D-tyrosyl-tRNA synthetase.

The presently claimed invention relates to products and methods for one of altering and enhancing the stereospecificity of an enzyme comprising introducing a stereospecific editing domain into the enzyme. According to additional embodiments the method further comprises increasing the effectiveness of the editing domain in the enzyme by decreasing the activity of a synthetic site in the enzyme. According to additional embodiments the method further comprises the step of producing D-stereospecific aminoacyl-tRNA synthetase. According to additional embodiments the method further comprises introducing an editing domain that stereospecifically hydrolyzes L-aminoacyl-tRNA isomers. According to additional embodiments the method further comprises causing one or more mutations to an aminoacyl-tRNA synthetase editing site, such that the editing site to substantially selectively hydrolyze L amino-acid isomers. According to additional embodiments the stereospecificity of the enzyme is enhanced, and the enzyme is an aminoacyl-tRNA synthetase. According to additional embodiments the method further comprises the steps of incorporating unnatural amino acids. According to additional embodiments the method further comprises introducing a hyperactive editing domain from phenylalanyl-tRNA synthetase into the aminoacyl-tRNA synthetase. According to additional embodiments introducing the stereospecific editing domain allows for the specific hydrolyzation of an unwanted stereoisomer. According to additional embodiments the enzyme is one of phenylalanyl-tRNA synthetase and a phenylalanyl-tRNA synthetase variant and further comprising the steps of increasing an activity of a phenylalanyl-tRNA synthetase editing domain. According to additional embodiments the method further comprises introducing multiple activating mutations into the phenylalanyl-tRNA synthetase editing domain. According to additional embodiments the method further comprises substantially simultaneously introducing multiple activating mutations into the phenylalanyl-tRNA synthetase editing domain. According to additional embodiments the enzyme is tyrosyl-tRNA synthetase. According to additional embodiments the method further comprises engineering the tyrosyl-tRNA synthetase to aminoacylate tRNAs with unnatural amino acids. According to additional embodiments the method further comprises introducing a phenylalanyl-tRNA synthetase editing domain containing multiple activating mutations into the engineered tyrosyl-tRNA synthetase.

The presently claimed invention further relates to products and methods of use and production of a mutant D-stereospecific tRNA synthetase enzyme comprising an aminoacyl-tRNA synthetase compound having one or more mutations in an editing site to substantially selectively hydrolyze L amino-acid isomers. According to additional embodiments the method further comprises the aminoacyl-tRNA synthetase compound having a plurality of mutations in the editing site to substantially selectively hydrolyze L amino-acid isomers.

The presently claimed invention further relates to products and methods of use and production of a manmade protein comprising at least one D-amino acid occupying an inverse conformational space. According to additional embodiments the method further comprises the at least one D-amino acid being used in place of a glycine residue. According to additional embodiments the method further comprises a plurality of D-amino acids.

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore the claimed invention should not necessarily be construed as limited to addressing any of the particular problems or deficiencies discussed herein.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which:

FIGS. 6A-6C show quantitation of the free energy of interaction for F145A and S211A alanine substitutions. Double mutant free energy cycles are shown for the interaction between the F145A and S211A substitutions in the TyrRS-FRSed editing domain. Standard free energies of interaction ($\Delta^2 G°_{int}$) are shown for the TyrRS•Tyr-tRNA$^{Tyr}$, TyrRS•[Tyr-tRNA$^{Tyr}$]$^‡$, and activation energy (FIGS. 6A-6C, respectively). Standard free energy changes ($\Delta G°$) for introducing each alanine substitution into the protein (e.g. F145/S211→F145A/S211) are next to the arrow for each transition. Standard free energies for each TyrRS-FRSed variant, relative to the unliganded enzyme, are shown next to the corresponding variant (e.g. $\Delta G°_{F145A/S211A}$=−31.9 kJ/mol for the TyrRS•L-Tyr-tRNA complex).

FIGS. 7A and 7D lie on opposite faces). Ternary standard free energies of interaction ($\Delta^3 G°_{int}$) are calculated from the difference between the $\Delta^2 G°_{int}$ values for double mutant free energy cycles on opposite faces of the cube (e.g. $\Delta^3 G°_{int} = \Delta^2 G°_{int,panel\ D} - \Delta^2 G°_{int,panel\ A} = -0.8$ kJ/mol). The S211 side chain is replaced by alanine in all of the variants.

FIG. 9A: wild-type TyrRS-FRSed (solid squares), the editing defective TyrRS-FRSed-N217A (circles), TyrRS-FRSed-F145A (diamonds), TyrRS-FRSed-L202A (hollow squares). FIG. 9B: TyrRS-FRSed-L210A (solid squares), TyrRS-FRSed-S211A (circles), TyrRS-FRSed-T221A (diamonds), TyrRS-FRSed-T236A (hollow squares). FIG. 9C: TyrRS-FRSed-F145A/S211A (solid squares), TyrRS-FRSed-L202A/S211A (circles), TyrRS-FRSed-S211A/T221 (diamonds), TyrRS-FRSed-F145A/L202A/S211A (hollow squares). FIG. 9D: TyrRS-FRSed-F145A/S211A/T221A (solid squares), TyrRS-FRSed-L202A/S211A/T221A (circles), TyrRS-FRSed-F145A/S202A/S211A/T221 (diamonds), TyrRS-FRSed-L202A/S211A/T221A/T236A (hollow squares). The data are fit to a first order exponential equation with linear offset.

FIGS. 12A-12C: Standard free energy cycles for the interaction between the L202A and S211A alanine substitutions. FIGS. 12D-12F: Standard free energy cycles for the interaction between the S211A and T221A substitutions. Standard free energy changes ($\Delta G°$) for introducing each wild type side chain into the protein are next to the arrow for each transition. Standard free energies for each TyrRS-FRSed variant, relative to the free energy, are shown next to the corresponding variant;

FIGS. 14A-14F shows quantitation of the ternary free energy of interaction between F145A, L202A, and T221A alanine substitutions for the activation energy. The six faces of the triple mutant free energy cube are shown for the effect that the interaction between the F145A, L202A, and T221A alanine substitutions has on the activation energy (FIGS. 14A-14F). Double mutant free energy cycles representing opposite faces of the cube are located in the same horizontal column (e.g. panels A and D lie on opposite faces). Ternary standard free energies of interaction ($\Delta^3 G^{\circ}_{int}$) are calculated from the difference between the $\Delta^2 G^{\circ}_{int}$ values for double mutant free energy cycles on opposite faces of the cube (e.g. $\Delta^3 G^{\circ}_{int} = \Delta^2 G^{\circ}_{int,panel\ D} - \Delta^2 G^{\circ}_{int,panel\ A} = -1.8$ kJ/mol). The S211 side chain is replaced by alanine in all of the variants.

DETAILED DESCRIPTION

Figure 1A:
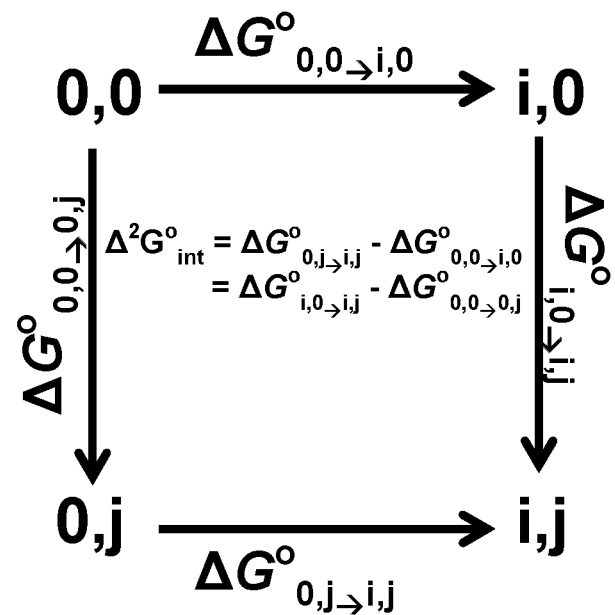
FIGS. 1A and 1B show hypothetical double mutant (FIG. 1A) and triple mutant (FIG. 1B) free energy cycles that can be used to calculate the effect that the interaction between two and three amino acid side chains has on a protein property (e.g. enzyme catalysis, protein stability). Wild type amino acid side chains are represented by i, j, and k, and replacement of the amino acid side chain by alanine is represented by 0. Standard free energies ($\Delta G°$) are calculated by subtracting the standard free energy for the species on the right (i.e. the product) from the species on the left (i.e. the substrate. Standard free energies of interaction are calculated from the difference in the $\Delta G°$ values for two opposing sides of the double mutant free energy cycle for secondary interactions ($\Delta^2 G°_{int}$) and from the difference in the $\Delta^2 G°_{int}$ values for two opposing sides of the triple mutant cube for ternary interactions ($\Delta^3 G°_{int}$).

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)–(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIGS. 1A-14F, a brief description concerning the various components of the present invention will now be briefly discussed.

Methods and Materials—

Materials were obtained from the following sources: TOPO TA cloning kit (Life Technologies, Grand Island, N.Y.), pET30(+) expression vector and BL21(DE3) *E. coli* cells (EMD Biosciences, Billerica, Miss.), XL2 Blue *E. coli* cells (Agilent, Santa Clara, Calif.), plasmid DNA Mini I kit (Omega Bio-Tek, Norcross, Ga.), T4 DNA ligase, NdeI, XhoI, and FokI (New England Biolabs, Ipswich, Mass.), HisPur NiNTA resin (Promega, Madison, Wis.), AMP and Biosafe II scintillation cocktail (Research Products International Corporation, Mount Prospect, Ill.), oligonucleotides (Integrated DNA Technologies, Coralville, Iowa), [$^{14}$C]L-tyrosine (Moravek, Brea, Calif.), and [$^{14}$C] and [$^{3}$H]D-tyrosine (American Radiochemicals, St. Louis, Mo.). All other reagents were obtained from VWR International or Fisher Scientific. DNA sequencing was performed by the Arizona State University DNA lab (Tempe, Ariz.). Curve fitting and graphing was performed using GraFit (Eriathicus Software, London, UK) and Kaleidagraph (Syngery Software, Reading, Pa.).

Construction of Expression Plasmids—

Construction of an expression plasmid for the TyrRS-FRSed chimera (the *Pyrococcus horikoshii* phenylalanyl-tRNA synthetase editing domain inserted into the CP1 domain of *Geobacillus stearothermophilus* tyrosyl-tRNA synthetase) is described in the manuscript included in the APPENDIX. This expression plasmid contains the TyrRS-FRSed coding sequence inserted into the pET30(a)+ vector and is designated pYF1-WT. Activating mutations were introduced into the phenylalanyl-tRNA synthetase editing domain by PCR overlap extension with KOD DNA polymerase to amplify the TyrRS-FRSed coding sequence. Variants with more than one amino acid replacement were introduced using pYF1-S211A as a template and carry the phenylalanyl-tRNA synthetase editing domain variant serine 211 to alanine (S211A). Individual PCR fragments were isolated via Promega SV gel purification and DNA clean up kit prior to recombination by PCR amplification using primers at the 5' and 3' ends of the tyrosyl-tRNA synthetase coding sequence. Following amplification by KOD DNA polymerase, the TyrRS-FRSed coding sequence was purified and A-tailed with Taq DNA polymerase and dATP at 72° C. for 10 minutes. The full length TyrRS-FRSed PCR products were then ligated into pCR2.1-TOPO using a TOPO TA cloning kit and transformed into XL2 Blue cells. Individual colonies were selected and grown overnight in 2 mL 2xYT (16 g/L tryptone, 10 g/L yeast extract, and 5 g/L NaCl) media, followed by PCR amplification to confirm the presence of the TyrRS-FRSed coding sequence. Plasmids from positive clones were isolated using a DNA Mini I kit and the insert was sequenced in its entirety. The TyrRS-FRSed coding sequences were then subcloned into the pET30a(+) expression vector using NdeI and XhoI restriction sites at the 5' and 3' ends respectively, such that the coding sequence is in frame with the coding sequence for a carboxyl-terminal 6×His-tag. Single mutation variants are labeled by their mutation according to the *P. horikoshii* phenylalanyl-tRNA synthetase nomenclature, and multiple mutants are labeled as the combination of single amino acids replacements (e.g. pYF1-S211A represents the expression plasmid for the TyrRS-FRSed chimera containing the S211A activating mutation in the phenylalanyl-tRNA synthetase editing domain). The specific mutations introduced into the phenylalanyl-tRNA synthetase were: F145A, L202A, L210A, S211A, T221A, T236A, F145A/S211A, L202A/S211A, T221A/S211A, F145A/L202A/S211A, F145A/T221A/S211A, L202A/T221A/S211A, F145A/L202A/T221A/S211A, and L202A/S211A/T221A/T236A.

Protein Expression and Purification—

*S. cerevisiae* AMP Deaminase, *S. cerevisiae* IMP dehydrogenase, T7 RNA polymerase, *S. cerevisiae* inorganic pyrophosphatase, wild-type *G. stearothermophilus* tyrosyl-tRNA synthetase, *T. thermophilus* D-tyrosyl-tRNA deacylase, and the TyrRS-FRSed chimera (both wild-type and editing domain variants were expressed and purified as described in the manuscript included in the APPENDIX. Briefly, purification of the TyrRS-FRSed chimera variants involved expression in *E. coli* BL21(DE3) cells and purification using NiNTA affinity chromatography. Proteins were isolated to >95% homogeneity based on SDS-PAGE. Extinction coefficients and molecular weights were calculated using the ExPASy ProtParam tool, as described in the manuscript included in the APPENDIX. The TyrRS-FRSed variants were stored in buffer containing 20 mM Tris, pH 7.8, 10 mM β-mercaptoethanol, 1 mM EDTA, and 20% glycerol.

In Vitro Transcription and Purification of tRNA$^{Tyr}$—

The *G. stearothermophilus* tRNA$^{Tyr}$ was synthesized by runoff transcription using T7 RNA polymerase using pGFX-WT as a template, as previously described. Briefly, the pGFX-WT, which contains the gene encoding *G. stearothermophilus* tRNA$^{Tyr}$ with a 5' T7 promoter and a 3' FokI restriction endonuclease site, was digested with FokI for 2 hours at 37° C. to create template for the in vitro transcription. Transcription reactions contained 100 mM HEPES pH 7.5, 20 mM MgCl$_2$, 40 mM DTT, 4 mM spermadine, 6.25 mM NTPs, 0.1 mg/mL BSA, 2 U/mL inorganic pyrophosphatase, 0.3 mg/mL T7 RNA polymerase, and 10 U/mL RNase inhibitor, and were incubated at 37° C. for 4 hours. tRNA was isolated using DE52 resin, ethanol precipitated, resuspended with 100 mM HEPES pH 7.5, and annealed by heating tRNA at 85° C. for 5 minutes, adding MgCl$_2$ to 10 mM, and cooling to room temperature. A nitrocellulose filter-binding aminoacylation assay was used to monitor the incorporation of [$^{14}$C]L-tyrosine, which forms L-tyrosyl-tRNA, and was compared to concentrations determined by A$_{260}$ ($\varepsilon_{260}$=806,100 M$^{-1}$ cm$^{-1}$), indicating that more than 70% of tRNA$^{Tyr}$ can be aminoacylated.

Aminoacylation Assay—

Aminoacylation reactions were performed as described in the manuscript included in the APPENDIX. Unless otherwise stated, assays contained 10 mM MgATP, 100 mM Tris pH 7.8, 10 mM MgCl$_2$, 2 U/mL inorganic pyrophosphatase, and either 10 µM [$^{14}$C]L-tyrosine or 25 µM [$^{14}$C]D-tyrosine with variable concentrations of TyrRS and tRNA$^{Tyr}$ (inorganic pyrophosphatase units are equivalent to those used by NEB for *T. litoralis* inorganic pyrophosphatase). The aminoacylation potential of tRNA$^{Tyr}$ was determined using a nitrocellulose filtration assay in which 1 µM tRNA (based on A$_{260}$ measurements) was incubated with 50 nM wild-type tyrosyl-tRNA synthetase. Samples were quenched by the addition of 3 mL 5% TCA and filtered through BA-85 nitrocellulose discs presoaked with 5% TCA. The nitrocellulose discs were washed three times with cold 5% TCA, dried, and scintillation counted to quantify the amount of [$^{14}$C]L-tyrosyl-tRNA bound to the disc.

Monitoring Trans-Editing of the Tyrosyl-tRNA$^{Tyr}$ Product—

Trans-editing of the L- and D-tyrosyl-tRNA products was monitored by preforming the [$^{14}$C]L- and D-tyrosyl-tRNA product and monitoring its hydrolysis via a nitrocellulose filter binding assay. [$^{14}$C]tyrosyl-tRNA$^{Tyr}$ was formed by incubating 100 nM TyrRS-WT, 10 mM MgATP, 5 µM tRNA$^{Tyr}$ and either 10 µM [$^{14}$C]L-tyrosine or 25 µM [$^{14}$C]D-tyrosine in the presence of 100 mM Tris, pH 7.8, 10 mM MgCl$_2$, and 2 U/mL inorganic pyrophosphatase at 25° C. for either 20 minutes (L-tyrosine) or 40 minutes (D-tyrosine). The [$^{14}$C]tyrosyl-tRNA product was purified by two phenol:chloroform:isoamylalcohol (50:49:1) extractions, followed by the addition of 0.5 volumes of 7.5 M ammonium acetate and ethanol precipitation. Dried pellets were resuspended in 100 mM HEPES, pH 7.5, 10 mM MgCl$_2$, and 5 µL aliquots were removed, spotted onto nitrocellulose filters, and scintillation counted to determine the concentration of [$^{14}$C]tyrosyl-tRNA$^{Tyr}$. Trans-editing activity was monitored by incubating [$^{14}$C]tyrosyl-tRNA (2-5 µM) with 50-250 nM TyrRS-WT or TyrRS-FRSed in the presence of 100 mM HEPES, pH 7.5, and 10 mM MgCl$_2$. 10 µL aliquots were removed and quenched by the addition to 3 mL 5% TCA, filtered through nitrocellulose discs to separate [$^{14}$C]tyrosyl-tRNA$^{Tyr}$ from [$^{14}$C]tyrosine, and scintillation counted to quantify the amount of [$^{14}$C]tyrosyl-tRNA$^{Tyr}$ bound to the disc. The data was plotted (cpm versus time) and fit a first order decay equation with floating endpoint:

$$[\text{TyrRS-tRNA}]_t = [\text{TyrRS-tRNA}]_0 e^{-k_1 t} + [\text{TyrRS-tRNA}]_\infty \quad \text{(Equation 1)}$$

where [TyrRS-tRNA]$_t$ is the concentration of [$^{14}$C]-labeled tyrosyl-tRNA$^{Tyr}$ at time t, [TyrRS-tRNA]$_0$ is the initial concentration of [$^{14}$C]-labeled tyrosyl-tRNA$^{Tyr}$ (i.e. at t=0), k$_1$ is the rate of hydrolysis, t is the time in seconds, and [TyrRS-tRNA]$_\infty$ is the final concentration of [$^{14}$C]-labeled [TyrRS-tRNA] (i.e. at an infinite time point).

Monitoring Editing of Tyrosyl-tRNA Produced In Situ—

The editing activity of the TyrRS-FRSed variants was monitored using a continuous spectrophotometric assay in which tyrosyl-tRNA is produced in situ. This assay is based on a continuous spectrophotometric tyrosyl-tRNA synthetase assay in which the production of AMP is coupled to the reduction of NAD$^+$, resulting in an increase in absorbance at 340 nm ($\varepsilon_{340}$=6220 M$^{-1}$ cm$^{-1}$). To monitor editing activity, wild-type tyrosyl-tRNA synthetase is used to generate tyrosyl-tRNA in situ, while the TyrRS-FRSed variant hydrolyzes the tyrosyl-tRNA product, regenerating the free tyrosine and tRNA substrates. If the wild-type tyrosyl-tRNA synthetase and TyrRS-FRSed concentrations are adjusted such that hydrolysis of tyrosyl-tRNA is the rate-limiting step in the reaction, then the increase in absorbance at 340 nm will correspond to the editing activity of the TyrRS-FRSed variant. Specifically, the spectrophotometric TyrRS-FRSed editing assay contained 50 mM Tris, pH 7.78, 10 mM KCl, 10 mM MgCl$_2$, 0.1 mM dithiothreitol, 10 mM MgATP, 5 mM NAD$^+$, 160 nM AMP deaminase, 640 nM IMP dehydrogenase, 2 U/mL inorganic pyrophosphatase, 0.5 mM tyrosine, 0.5-1 µM TyrRS-WT and 50-250 nM TyrRS-FRSed, and variable concentrations of tRNA$^{Tyr}$. All substrate solutions were adjusted to pH 7.0 prior to use. Assays were either 100 or 200 µL in volume (corresponding to 0.28 and 0.56 cm pathlengths, respectively) and were performed in 96-well plates at 25° C. Changes in absorbance at 340 nm were monitored using a Biotek Synergy 4 plate reader. The changes in absorbance were plotted against time and fit to a linear equation to determine the initial rate ($v_o$) for each substrate concentration.

Initial rates ($A_{340}$/sec) were converted to µmol/sec Beer's law (A=εbc, where A is the absorbance ε is the molar extinction coefficient, and b is the sample path length, and c is the molar concentration). Rates were plotted against substrate concentration and the data was fit to the Michaelis-Menten equation to determine the $K_M$ and $V_{max}$ values:

$$v_0 = V_{max}[S]/(K_M + [S]) \quad \text{(Equation 2)}$$

where $v_0$ is the initial rate, $V_{max}$ is the maximum rate, [S] is the substrate concentration, and $K_M$ is the Michaelis constant for the substrate.

The $k_{cat}$ values were calculated from $V_{max}$ using the equation 3:

$$V_{max} = k_{cat}[E] \quad \text{(Equation 3)}$$

where [E] is the total enzyme concentration.

Calculation of Relative Free Energies—

The relative free energies for the binding of L-tyrosyl-tRNA$^{Tyr}$ to the phenylalanyl-tRNA synthetase editing domain of the TyrRS-FRSed chimera and subsequent formation of the TyrRS-FRSed•[Tyr-tRNA]$^‡$ transition state were calculated from $K_M$ and $k_{cat}$ values determined in the spectrophotometric assay, assuming standard states of 1 M tyrosyl-tRNA as follows:

$$G_{E\cdot Tyr\text{-}tRNA} = -RT \ln(K_M) \quad \text{(Equation 4)}$$

$$G_{E\cdot [Tyr\text{-}tRNA]‡} = RT \ln(k_B T/h) - RT \ln(k_{cat}/K_M) \quad \text{(Equation 5)}$$

where $G_{E\cdot Tyr\text{-}tRNA}$ and $G_{[E\cdot Tyr\text{-}tRNA]‡}$ are the Gibbs free energy values for TyrRS-FRSed•Tyr-tRNA and TyrRS-FRSed•[Tyr-tRNA]$^‡$ complexes relative to that of the unliganded TyrRS-FRSed, R is the gas constant, T is the absolute temperatures, $k_B$ is the Boltzmann constant, h is Planck's constant, "•" and "–" denote noncovalent and covalent bonds, respectively. Subtracting equation 7 from equation 8 results in the following equation:

$$G_{[E\cdot Tyr\text{-}tRNA]‡} = -RT \ln(k_B T/h) - RT \ln(k_{cat}) \quad \text{(Equation 6)}$$

which was used to calculate the Gibbs activation energy.

Calculation of Interaction Energies—

Synergistic and antisynergistic interactions between editing site resides were quantified by calculating the Gibbs free energies of interaction using the convention described previously (First and Fersht, 1995). Briefly, this involves calculating the binding energy for each complex relative to the free energy of the unliganded enzyme (i.e. $G_E=0$) as described above and in (Wells and Fersht, 1986). The apparent binding energy for side chain that has been mutated ($\Delta G_{app}$) is calculated by subtracting the free energy change for formation of the complex by the wild-type enzyme from that of the variant enzyme (e.g. $\Delta G_{app} = G_{E\cdot Tyr\text{-}tRNA}$(mutant)–$G_{E\cdot Tyr\text{-}tRNA}$(wild-type), where $G_{E\cdot Tyr\text{-}tRNA}$ for the mutant and wild-type enzymes are calculated using equation 4, as described above). To quantify the effect that the interaction between two residues has on the binding of a particular complex, double mutant free energy cycles are constructed and the pairwise interaction energy ($\Delta^2 G_{int}$) is calculated as described by Horovitz and Fersht (1992), using the following equation:

$$\Delta^2 G_{int} = \Delta G_2 - \Sigma \Delta G_1 \quad \text{(Equation 7)}$$

where $\Delta G_1$ is the free energy change for the addition of one sidechain in the absence of the other side chain and $\Delta G_2$ is the free energy for the addition of both side chains simultaneously. Similarly, the ternary coupling interaction energies (i.e. the effect of a third side chain on the previous pairwise coupling interaction between the first two residues) can be calculated using the following equation:

$$\Delta^3 G_{int} = \Delta G_3 - \Sigma \Delta G_2 + \Sigma \Delta G_1 \quad \text{(Equation 8)}$$

where $\Delta G_1$ and $\Delta G_2$ are as described above and $\Delta G_3$ is the free energy for adding all three sidechains simultaneously (Horovitz and Fersht, 1992).

Propagation of Errors—

Errors in primary data were determined by calculating the standard error, based on at least three independent experiments. For subsequent calculations (e.g. $k_{cat}/K_m$, $\Delta G°$, $\Delta^2 G°_{int}$, etc.), errors were propagated using the equations shown below.

For addition or subtraction (x+y=R):

$$dR = \sqrt{(dx)^2 + (dy)^2} \quad \text{(Equation 9)}$$

where x and y are the variables (e.g. $k_{cat}$, $K_m$, $\Delta G°$, etc.), R is the final result, and dx, dy, and dR are the errors in x, y, and R.

For multiplication or division of two variables (x·y=R):

$$dR = |R|\sqrt{(dx/x)^2 + (dy/y)^2} \quad \text{(Equation 10)}$$

where x, y, R, dx, dy, and dR are defined above.

For multiplication or division by a constant value (c·x=R):

$$dR = |c| \cdot dx \quad \text{(Equation 11)}$$

where c is a constant and x, R, and dR are defined above.

For conversion to a natural logarithm (ln(x)=R):

$$dR = dx/x \quad \text{(Equation 12)}$$

where x, R, dx, and dR are defined above.

Monitoring the Competition Between L- and D-Tyrosine—

A competition assay was used to quantify the effect that introducing the phenylalanyl-tRNA synthetase editing domain into tyrosyl-tRNA synthetase had on the stereospecificity of the enzyme. Competition assays contained 10 mM MgATP, 100 mM Tris pH 7.8, 10 mM MgCl$_2$, 1 U/mL inorganic pyrophosphatase, 10 µM tRNA, 50-200 nM TyrRS-FRSed, 30 µM [$^{14}$C]L-tyrosine, and variable concentrations of [$^3$H]D-tyrosine (0 to 120 µM). Assays were incubated at 25° C. for 15 minutes, at which point 20 µL aliquots were removed and were quenched by the addition to 3 mL 5% TCA. This 15 minute time point was selected based on the observation that this time point was within the linear phase of the reaction for both the TyrRS-WT and TyrRS-FRSed enzymes.

Following quenching of the reaction, the aliquots were filtered through nitrocellulose filters that had been presoaked in 5% TCA. The nitrocellulose filters were washed three times with 3 mL of ice-cold 5% TCA, dried, and subjected to scintillation counting to quantify the amount of [$^{14}$C]L-tyrosyl-tRNA and [$^3$H]D-tyrosyl-tRNA present. The Beckman LS-6500 scintillation counter was calibrated using commercial standards (Beckman Coulter), and quench curves for the dual label counting were setup by spotting [$^{14}$C]L-tyrosine and [$^{3}$H]D-tyrosine onto nitrocellulose filters, adding 5.5 mL Biosafe II scintillation cocktail to 7 mL scintillation vials, and adding increasing amounts of chloroform to the vials. Counting efficiencies for [$^{3}$H]D-tyrosine were near 40%, while efficiencies for [$^{14}$C]L-tyrosine were greater than 85%, compared to the calculated DPMs. After normalizing for counting efficiency, the data were plotted as [D-Tyr-tRNA]/[L-Tyr-tRNA] vs. [D-tyrosine] and fit to a linear equation.

Theory—

For all naturally occurring amino acids except glycine and alanine, substitution of the side chain by alanine effectively removes that amino acid side chain. This allows one to use alanine substitution to determine the role that specific amino acids play in the properties of a protein (e.g. enzyme catalysis, protein folding, etc.). Alanine substitutions usually represent a relatively conservative change as it is less likely that adventitious effects will result from removal of a side chain than would be the case if the side chain was replaced with another side chain that alters its chemical or steric properties. The effect that the side chain has on catalysis (or another property, such as stability) can be quantified by converting the rate and dissociation (or Michaelis) constants to standard Gibbs free energy values for the wild type and alanine substituted enzymes. This is done by calculating the free energy change for the wild type and alanine substituted protein variants (e.g. using $\Delta G^\circ = -RT\ln K_{eq}$, or an analogous equation) and then subtracting the standard free energy change of the alanine variant from that of the wild type protein (i.e. $\Delta G^\circ_{0 \to i}$, where i is the wild type side chain and 0 is the alanine substitution).

Figure 1B:
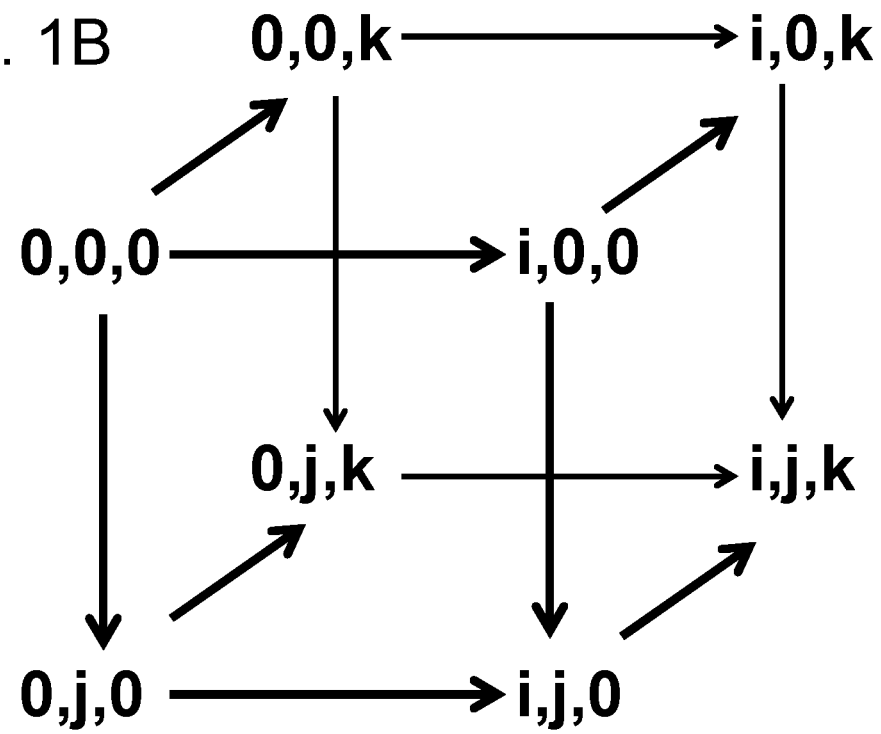
Figure 2:
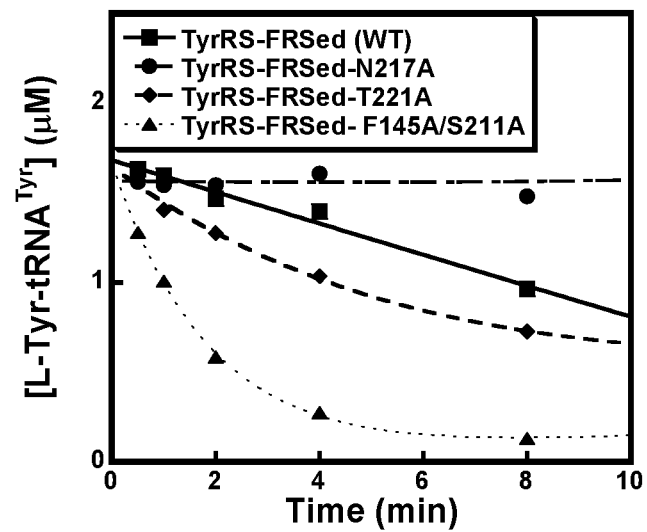
FIG. 2 shows trans-editing of L-Tyr-tRNA$^{Tyr}$ by alanine variants of the TyrRS-FRSed. Representative plots for the hydrolysis of L-[$^{14}$C]Tyr-tRNA$^{Tyr}$ are shown for selected TyrRS-FRSed editing domain variants. TyrRS-FRSed variants shown are the wild-type TyrRS-FRSed (squares), the editing defective TyrRS-FRSed-N217A variant (circles), the TyrRS-FRSed-T221A variant (diamonds), and the TyrRS-FRSed-F145A/S211A variant (triangles). The data are fit to a first order exponential equation with linear offset.

As interactions between amino acids play an essential role in a protein's properties, it is of interest to quantify not only the effect that a single amino acid side chain has on the protein, but also the effect due to the interaction between amino acid side chains. This can be done by introducing alanine substitutions at multiple positions and quantifying the effect that these substitutions have using multimutant free energy cycles. For example, a double mutant free energy cycle can be used to quantify the role that the interaction between two amino acids plays in a protein's property (e.g. enzyme catalysis). This is shown in FIG. 1, panel A where i and j represent the wild type side chains at two different amino acid positions in the protein and 0 represents the alanine substitutions at these positions.

Comparing the transformations at the top and bottom of the double mutant free energy cycle (i.e. 0,0→i,0 and 0,j→i,j, respectively) one can see that the only difference between the two transformations is the absence (top) or presence (bottom) of the second side chain (j). In other words, the difference between the standard free energies for the two transformations is due to the standard free energy of interaction between the i and j side chains (i.e. $\Delta^2 G^\circ_{int}$). The value of $\Delta_2 G^\circ_{int}$ can be calculated by subtracting the standard free energy changes for opposite sides of the cycle (FIG. 1, panel A). Alternatively, one can use equation 9 to calculate $\Delta^2 G^\circ_{int}$. For alanine substitutions that decrease the activity (or other property) of the protein, drawing the free energy cycle with the double alanine variant in the upper left hand corner of the cycle and the wild type enzyme in the lower right hand corner, results in $\Delta^2 G^\circ_{int} < 0$ if the interaction between the i and j side chain is synergistic and $\Delta^2 G^\circ_{int} > 0$ if the interaction is antisynergistic. If $\Delta^2 G^\circ_{int} = 0$, this indicates that there is no interaction between the side chains (i.e. the effect of adding the two wild type side chains is additive).

Multimutant free energy cycles can be extended to higher orders to quantify interactions between three or more amino acid side chains. This is shown in FIG. 1, panel B where a triple mutant free energy cube is used to quantify the free energy changes associated with alanine substitutions at three amino acid positions. Comparing two opposing faces of the cube, one can see that the only difference between the two double mutant free energy cycles is the absence or presence of the third amino acid (e.g. amino acid k in the front and back faces). In other words, the only difference between $\Delta^2 G^\circ_{int}$ for the two double mutant free energy cycles is whether the third amino acid side chain is absent or present. As a result, the difference between the $\Delta^2 G^\circ_{int}$ values for the two cycles ($\Delta^3 G^\circ_{int}$) represents the effect that the third amino acid side chain has on the standard free energy of interaction for the other two residues (i.e. the $\Delta^2 G^\circ_{int}$ value). For example, comparing the front and back faces in FIG. 1, panel B, $\Delta^3 G^\circ_{int}$ represents the effect that the side chain of amino acid k has on the interaction between the side chains of amino acids i and j. Since free energy is a state function, the $\Delta^3 G^\circ_{int}$ values are identical for the three pairs of double mutant free energy cycles. Using the same frame of reference as was used for the double mutant free energy cycles, $\Delta^3 G^\circ_{int}$ is calculated by subtracting the $\Delta^2 G^\circ_{int}$ value for the front cycle (i.e. the cycle containing more alanine substitutions) from the $\Delta^2 G_{int}$ value for the back cycle (i.e. the cycle containing fewer alanine substitutions). This is mathematically equivalent to equation 10 and results in $\Delta^3 G^\circ_{int} < 0$ for synergistic interactions (i.e. the third residue has a synergistic effect on the interaction between the other two residues) and $\Delta^3 G^\circ_{int} > 0$ for antisynergistic interactions. In general, one can calculate the standard free energy of interaction for any dimension using the equation:

$$\Delta^n G_{int} = \sum_{r=1}^{n} (-1)^{r+n} \sum_{\alpha=1}^{n_r} \Delta G_{r,\alpha}$$

(Equation 19)

where n is the total number of side chains being added, r is the number of additions in a given molecule (r≤n), $n_r$ are the binomial coefficients, and α represents the different possible combinations for each r value.

Free energy analysis of amino acid substitutions that result in a more active protein is similar to that used to monitor deleterious substitutions, except that the frame of reference is reversed. In other words, for substitutions that increase the activity (or other property) of a protein, the most active variant is located in the bottom right corner of the cycle (i.e. where the wild type protein would normally be located). Using this convention, the $\Delta^2 G^\circ_{int} < 0$ for interactions that have a synergistic effect on the activity (or other property) of the protein and $\Delta^2 G^\circ_{int} > 0$ for interactions that have an antisynergistic effect.

RESULTS—Editing Domain Mutations Activate Hydrolysis of L-Tyrosyl-tRNA, but not D-Tyrosyl-tRNA in the TyrRS-FRSed Variant.

Alanine substitutions near the hydrolytic active site of the *P. horikoshii* phenylalanyl-tRNA synthetase editing domain have been previously implicated in a loss of specificity of the editing domain. Since the insertion of this editing domain into tyrosyl-tRNA synthetase altered the stereospecificity of tyrosyl-tRNA synthetase, the inventors hypothesized that introducing phenylalanyl-tRNA synthetase editing domain variants containing these activating amino acid replacements into tyrosyl-tRNA synthetase, while leaving the synthetic active site of tyrosyl-tRNA synthetase unaffected, would further enhance the stereospecificity of the TyrRS-FRSed enzyme.

Figure 11A:
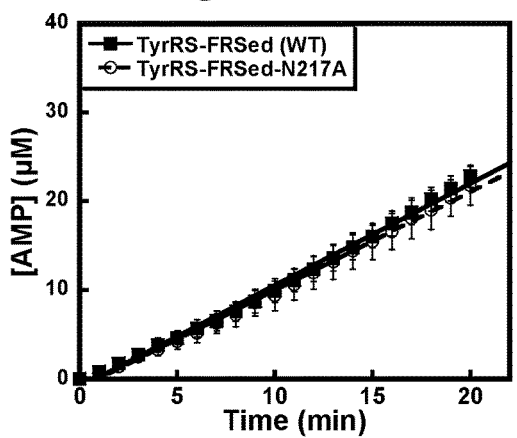
FIGS. 11A-11O show steady-state kinetic analysis of D-Tyr-tRNA$^{Tyr}$ hydrolysis by the TyrRS-FRSed variants. Representative plots for the hydrolysis of D-Tyr-tRNA$^{Tyr}$ by the TyrRS-FRSed variants (50 nM) is shown for D-tyrosyl-tRNA$^{Tyr}$ (generated in situ using 300 μM D-tyrosine and 6 μM tRNA$^{Tyr}$). Hydrolysis of D-tyrosyl-tRNA$^{Tyr}$ was monitored using the coupled assay shown in FIG. 3. The data are fit to a linear equation to determine the initial rate. Steady-state kinetics are shown for the wild-type TyrRS-FRSed (FIG. 11A), TyrRS-FRSed-F145A (FIG. 11B), TyrRS-FRSed-L202A (FIG. 11C), TyrRS-FRSed-L210A (FIG. 11D), TyrRS-FRSed-S211A (FIG. 11E), TyrRS-FRSed-T221A (FIG. 11F), TyrRS-FRSed-T236A (FIG. 11G), TyrRS-FRSed-F145A/S211A (FIG. 11H), TyrRS-FRSed-L202A/S211A (FIG. 11I), TyrRS-FRSed-S211A/T221A (FIG. 11J), TyrRS-FRSed-F145A/L202A/S211A (FIG. 11K), TyrRS-FRSed-F145A/S211A/T221A (FIG. 11L), TyrRS-FRSed-L202A/S211A/T221A (FIG. 11M), TyrRS-FRSed-F145A/L202A/S211A/T221A (FIG. 11N), and TyrRS-FRSed-L202A/S211A/T221A/T236A (FIG. 11O) variants.
Figure 11B:
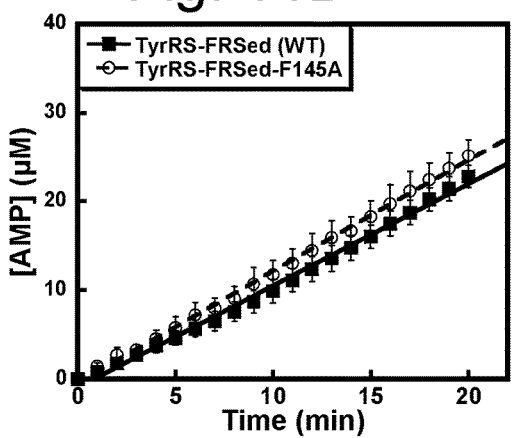
Figure 11C:
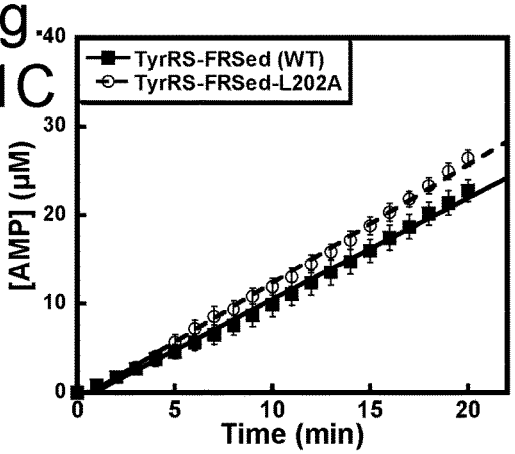
Figure 11D:
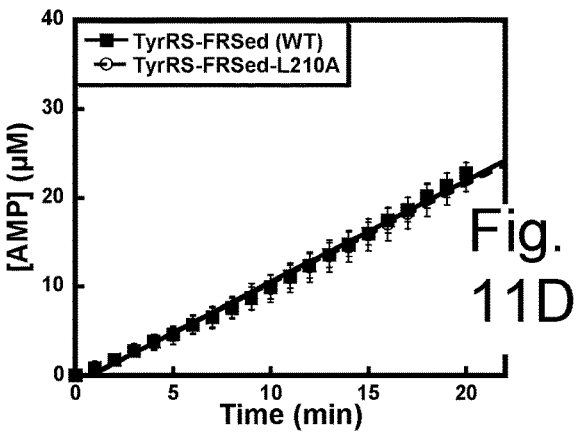
Figure 11E:
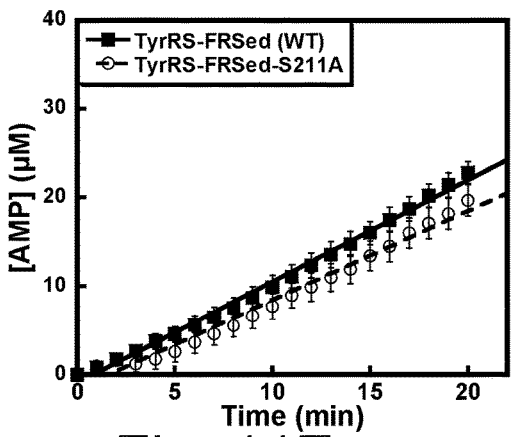
Figure 11F:
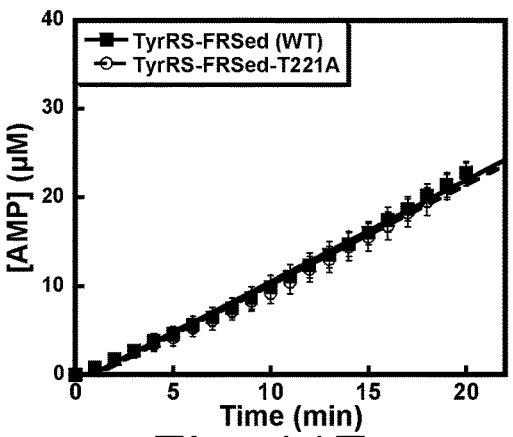
Figure 11M:
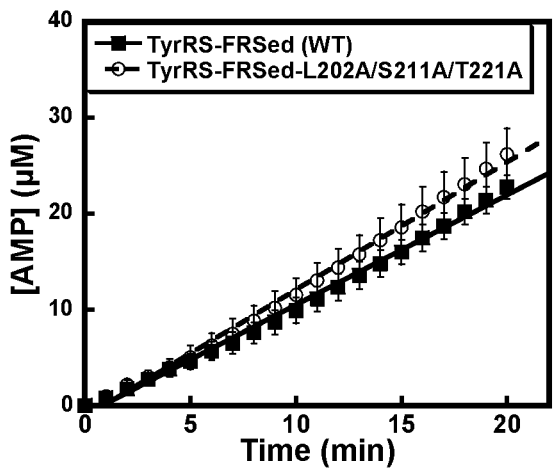
Figure 11N:
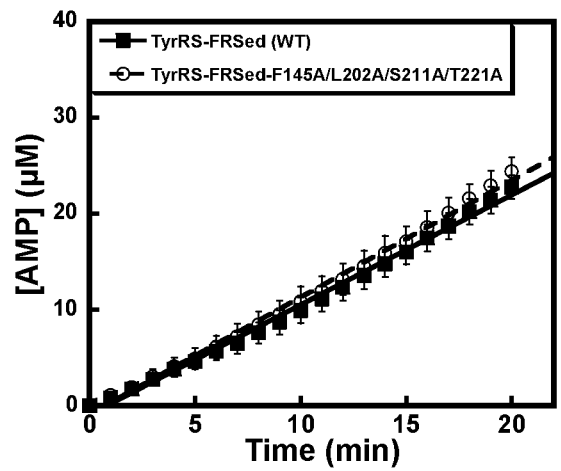
Figure 11O:
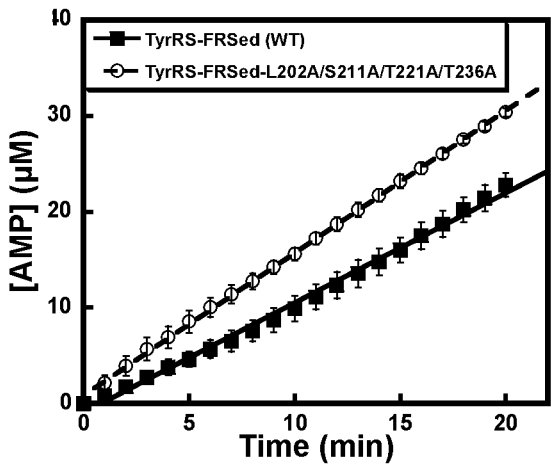
Figure 12A:
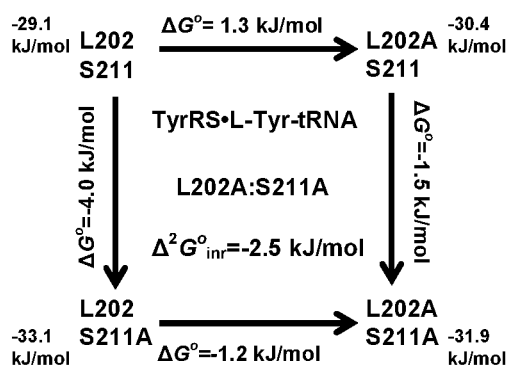
FIGS. 12A-12F show quantitation of the free energies of interaction for the E•L-Tyr-tRNA$^{Tyr}$ complex, E•[L-Tyr-tRNA$^{Tyr}$]$^‡$ transition state, and activation energy. Double mutant free energy cycles for the E•L-Tyr-tRNA$^{Tyr}$ complex, E•[L-Tyr-tRNA$^{Tyr}$]$^‡$ transition state, and activation energy.
Figure 12D:
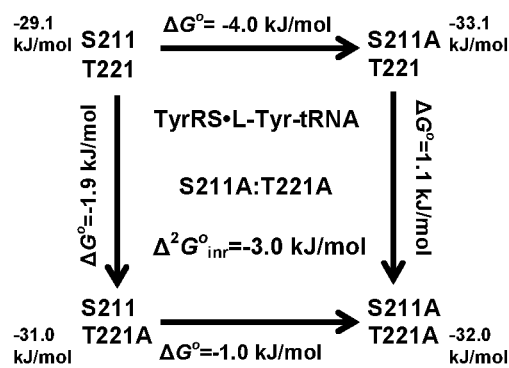
Figure 12B:
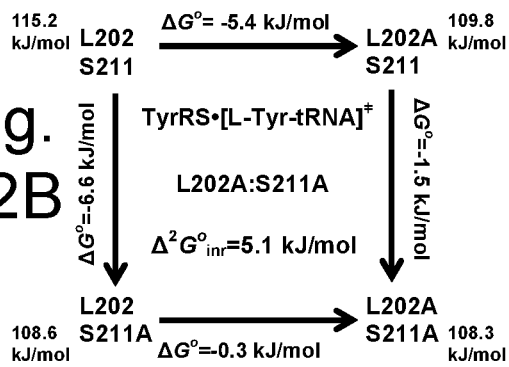
Figure 12E:
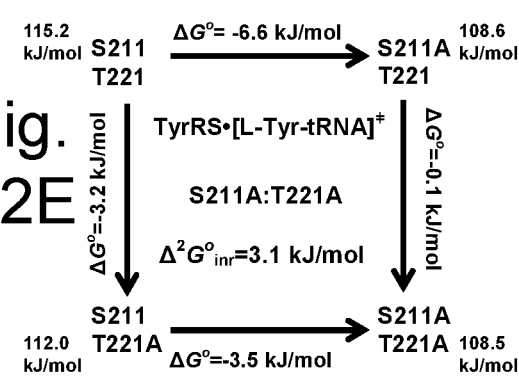
Figure 12C:
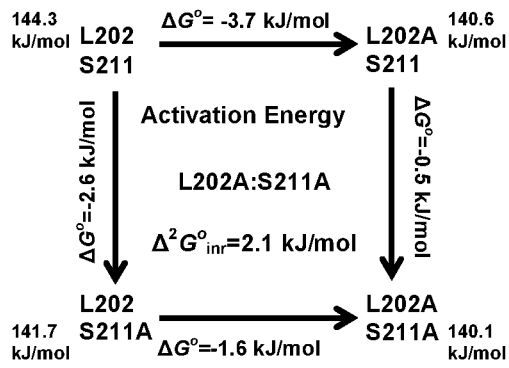
Figure 12F:
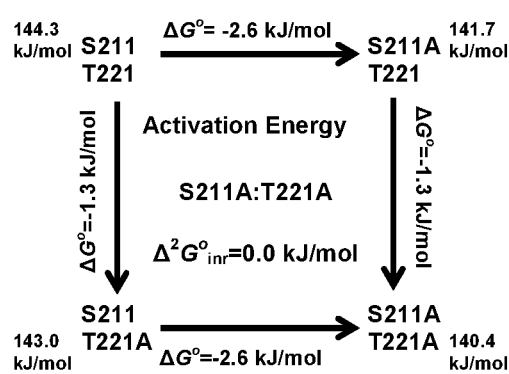
Figure 13A:
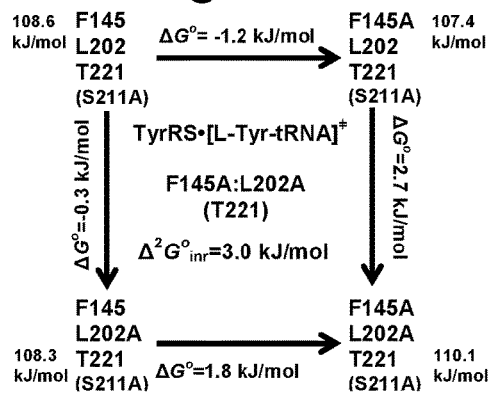
FIGS. 13A-13F show quantitation of the ternary free energy of interaction between F145A, L202A, and T221A alanine substitutions for the TyrRS•[L-Tyr-tRNA$^{Tyr}$]$^{\ddagger}$ transition state. The six faces of the triple mutant free energy cube are shown for the interaction between the F145A, L202A, and T221A alanine substitutions in the TyrRS•[L-Tyr-tRNA$^{Tyr}$]$^{\ddagger}$ transition state (FIGS. 13A-13F). Double mutant free energy cycles representing opposite faces of the cube are located in the same horizontal column (e.g. panels A and D lie on opposite faces). Ternary standard free energies of interaction ($\Delta^3 G_{int}$) are calculated from the difference between the $\Delta^2 G_{int}$ values for double mutant free energy cycles on opposite faces of the cube (e.g. $\Delta^3 G^{\circ}_{int} = \Delta^2 G^{\circ}_{int,panel\ D} - \Delta^2 G^{\circ}_{int,panel\ A} = -1.6$ kJ/mol). The S211 side chain is replaced by alanine in all of the variants.
Figure 13D:
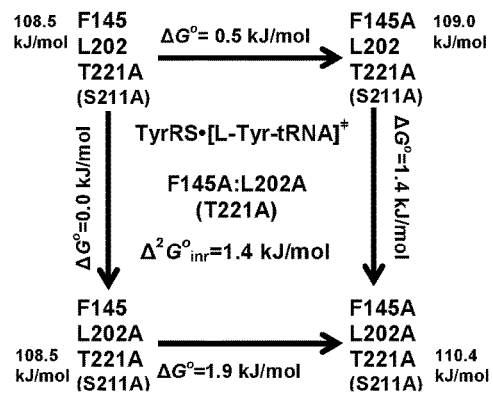
Figure 13B:
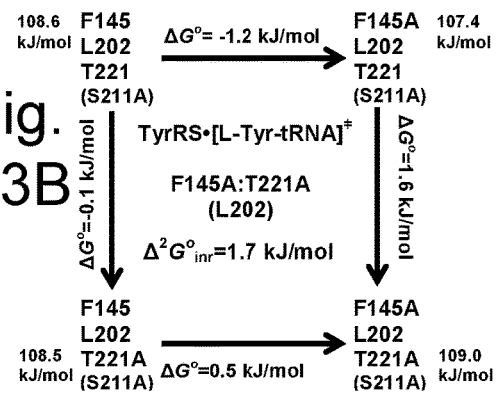
Figure 13E:
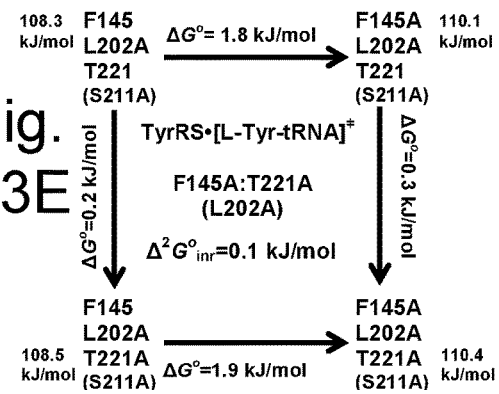
Figure 13C:
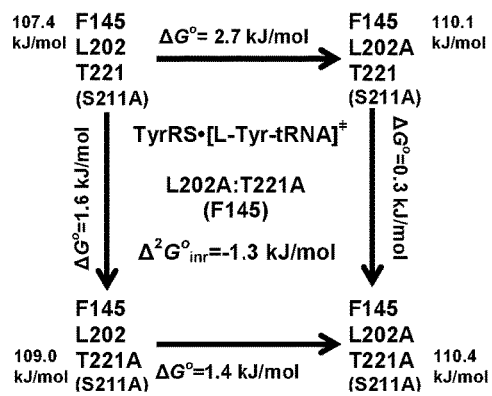
Figure 13F:
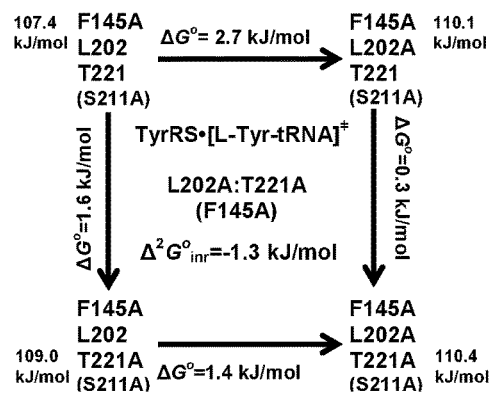

Six amino acid substitutions in the editing domain of *P. horikoshii* phenylalanyl-tRNA synthetase, F145A, L202A, L210A, S211A, T221A, and T236A (collectively the Yokoyama mutations) were introduced into the phenylalanyl-tRNA synthetase editing domain in the TyrRS-FRSed variant, both individually and in various combinations, as shown in Table 1. The inventors included the S211A substitution in all of the TyrRS-FRSed variants containing multiple activating substitutions. To determine the effect that these substitutions have on hydrolysis of L- and D-tyrosyl-tRNA$^{Tyr}$, a trans-editing assay was used. In this assay, each of the TyrRS-FRSed variants is incubated with [$^{14}$C]L-tyrosyl-tRNA$^{Tyr}$ at 25° C. At various time points, aliquots are removed, the hydrolysis reaction is quenched, and the samples are filtered through nitrocellulose discs to capture [$^{14}$C]L-tyrosyl-tRNA$^{Tyr}$ that has not been hydrolyzed. First order rate constants for hydrolysis of L-tyrosyl-tRNA$^{Tyr}$ by the TyrRS-FRSed editing domain variants are shown in Table 1 and FIGS. 9A-9D. All of the TyrRS-FRSed editing domain variants were more active towards L-tyrosyl-tRNA$^{Tyr}$ than the TyrRS-FRSed containing the wild-type editing domain (henceforth referred to as wild-type TyrRS-FRSed). Furthermore, as shown in FIGS. 11A-11O, the inability of the variants to hydrolyze [$^{14}$C]D-tyrosyl-tRNA$^{Tyr}$ indicated that all of these variants have retained their stereospecificity Steady-State Kinetic Analysis of L-Tyrosyl-tRNA$^{Tyr}$ Hydrolysis by the TyrRS-FRSed Editing Domain Variants.

While the trans-editing assay was useful for preliminary screening of the TyrRS-FRSed editing domain variants, using it for detailed kinetic analyses of each of the variants is both time-consuming and expensive. As an alternative to the trans-editing assay, the inventors developed a continuous spectrophotometric editing assay based on a high-throughput tyrosyl-tRNA synthetase assay that was recently developed in their laboratory (provisional patent application #62/060,059). Tyrosyl-tRNA synthetase catalyzes the aminoacylation of tRNA using a two-step mechanism. In the first step, tyrosine is activated by ATP, forming an enzyme-bound tyrosyl-adenylate intermediate (TyrRS•Tyr-AMP, where "•" and "–" represent noncovalent and covalent bonds, respectively). In the second step of the reaction, the tyrosyl moiety is transferred to the 3' end of tRNA$^{Tyr}$ and the Tyr-tRNA$^{Tyr}$ and AMP products are released from the enzyme. To monitor tyrosyl-tRNA synthetase activity, the production of AMP is coupled to the reduction of NAD$^{+}$ through the actions of AMP deaminase (which converts AMP to IMP) and IMP dehydrogenase (which uses NAD$^{+}$ to oxidize IMP to XMP). As reduction of NAD$^{+}$ to NADH results in an increase in absorbance at 340 nm ($\varepsilon_{340}^{NADH}$=6220 M$^{-1}$ cm$^{-1}$), tyrosyl-tRNA synthetase activity can be monitored spectrophotometrically. To increase the sensitivity and decrease the cost of the tyrosyl-tRNA synthetase assay, cyclodityrosine synthase is used to regenerate the tRNA$^{Tyr}$ substrate in situ. Cyclodityrosine synthase converts two molecules of L-tyrosyl-tRNA$^{Tyr}$ to cyclodityrosine and two molecules of tRNA$^{Tyr}$.

Figure 3:
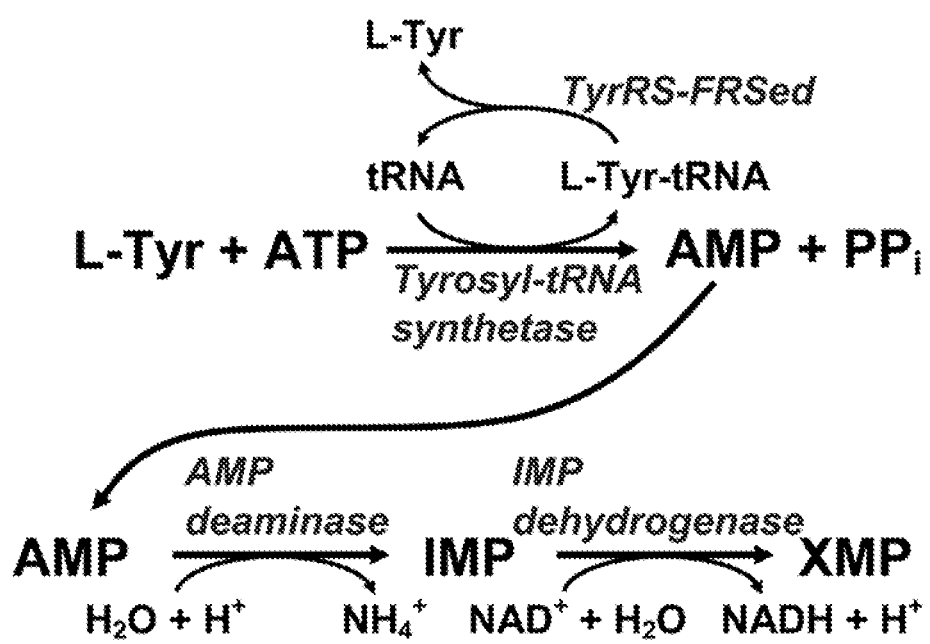
FIG. 3 shows reaction scheme for the L-tyrosyl-tRNA$^{Tyr}$ editing assay. The reaction scheme for coupling hydrolysis of L-tyrosyl-tRNA$^{Tyr}$ by TyrRS-FRSed to the production of NADH is shown. In this assay, L-tyrosyl-tRNA$^{Tyr}$ is generated in situ by tyrosyl-tRNA synthetase. Cleavage of L-tyrosyl-tRNA$^{Tyr}$ is catalyzed by the TyrRS-FRSed variant and is the rate-limiting step in the assay. L-Tyr, AMP, IMP, XMP, and PP$_i$ represent L-tyrosine, adenosine 5'-monophosphate, inosine 5'-monophosphate, xanthine 5'-monophosphate, and inorganic pyrophosphate, respectively.
Figure 4A:
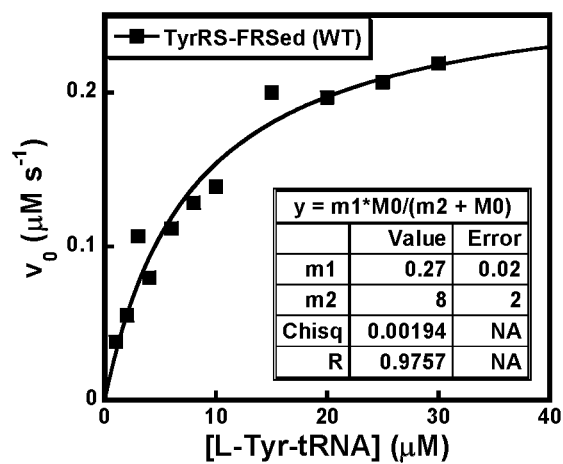
FIGS. 4A-4D show steady-state kinetic analysis of editing activity for TyrRS-FRSed variants. Representative steady-state kinetic plots of editing activity are shown for selected TyrRS-FRSed variants. Hydrolysis of L-tyrosyl-tRNA$^{Tyr}$ was monitored using the coupled assay shown in FIG. 3. The data are fit to the Michaelis-Menten equation (equation 2). Steady-state kinetics are shown for the wild-type TyrRS-FRSed (FIG. 4A), TyrRS-FRSed-F145A (FIG. 4B), TyrRS-FRSed-S211A (FIG. 4C), and TyrRS-FRSed-F145A/S211A (FIG. 4D) variants.
Figure 4B:
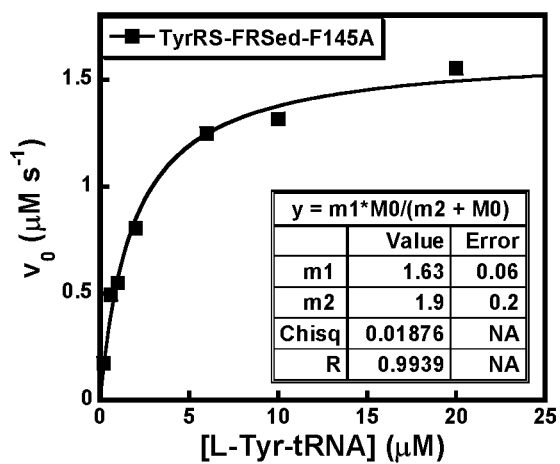
Figure 4C:
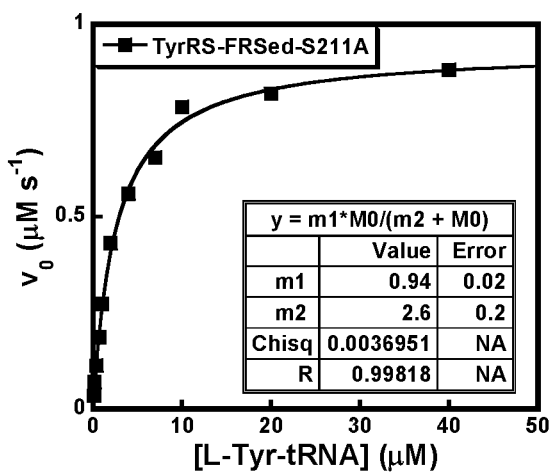
Figure 4D:
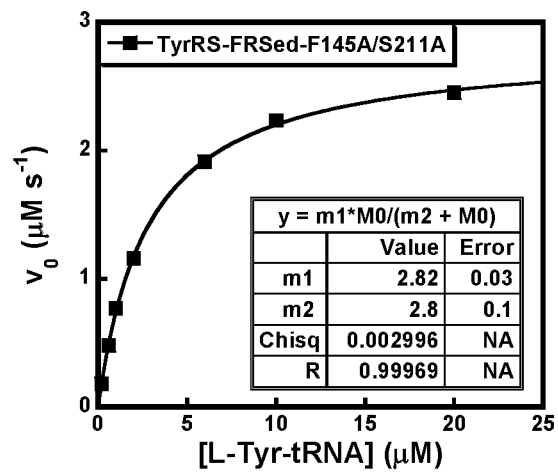

Turning next to FIG. 3, to adapt the above tyrosyl-tRNA synthetase assay for use in monitoring aminoacyl-tRNA synthetase editing activity, cyclodityrosine synthase was replaced by the editing domain variant (specifically either wild type TyrRS-FRSed or one of the editing domain variants). Synthesis of L-tyrosyl-tRNA$^{Tyr}$ is the rate-limiting step in the tyrosyl-tRNA synthetase assay. By contrast, in the editing assay, the relative concentrations of wild type tyrosyl-tRNA synthetase (with no editing domain) and the TyrRS-FRSed variant were adjusted such that hydrolysis of the L-tyrosyl-tRNA$^{Tyr}$ product was rate-limiting. As a result, L-tyrosyl-tRNA$^{Tyr}$ was generated in situ in this assay, allowing $K_m^{L-Tyr-tRNA}$ and $k_{cat}$ values to be determined by monitoring the initial rate at varying concentrations of tRNA$^{Tyr}$. This assay is amenable to a 96-well plate format, facilitating both rapid and precise analysis of L-tyrosyl-tRNA$^{Tyr}$ editing by the TyrRS-FRSed variants.

As shown in Table 1, FIG. 4, and FIGS. 10A-10K, to determine the rate ($k_{cat}$) and Michaelis ($K_m^{L-Tyr-tRNA}$) constants for each of the editing domain variants, the initial rate was determined at varying tRNA$^{Tyr}$ concentrations using the spectrophotometric editing assay described above. With the exception of T236A variant, all of the single variants increased the affinity of the editing domain for L-tyrosyl-tRNA$^{Tyr}$, with the S211A substitution having the largest effect on $K_m^{L-Tyr-tRNA}$. Comparing the steady state editing assay developed by the inventors with the results of the [14C]L-Tyr-tRNA hydrolysis experiments indicates that the two methods for measuring the initial rate for L-Tyr-tRNA hydrolysis give essentially identical results (Table 2 and Supplemental Table S1). This confirms that the editing assay developed by the inventors can be used to monitor post-transfer editing in aminoacyl-tRNA synthetases.

Much to the surprise of the inventors, introducing additional mutations in the presence of the S211A substitution decreased the affinity of the editing domain for L-tyrosyl-tRNA$^{Tyr}$ relative to that of TyrRS-FRSed containing only the S211A substitution. However, the TyrRS-FRSed variants containing multiple mutations still had a higher affinity for L-tyrosyl-tRNA$^{Tyr}$ than wild type TyrRS-FRSed. As shown in Table 1, analysis of $k_{cat}$ values for L-tyrosyl-tRNA hydrolysis indicated that all of the single mutants had higher values than the wild-type TyrRS-FRSed, with the F145A and L202A variants having the largest $k_{cat}$ values of all the single mutants. Introducing a second mutation in the TyrRS-FRSed-S211A variant, resulted in an increase in $k_{cat}$ values, with the F145A/S211A double mutant displaying the highest $k_{cat}$ value. Introducing additional substitutions beyond the second mutation decreased the $k_{cat}$ value for the editing domain (although the $k_{cat}$ values for the triple and quadruple mutants were still higher than that of the wild-type TyrRS-FRSed).

In the APPENDIX manuscript, the inventors showed that the wild-type phenylalanyl-tRNA synthetase editing domain is stereospecific, catalyzing the hydrolysis of L-tyrosyl-tRNA$^{Tyr}$, but not D-tyrosyl-tRNA$^{Tyr}$. To determine whether this stereospecificity is lost in the editing domain variants, time course assays were performed using saturating D-tyrosine and tRNA$^{Tyr}$ concentrations (300 µM and 6 µM, respectively) using the continuous spectrophotometric phenylalanyl-tRNA synthetase editing assay. As shown in FIGS. 11A-11O, no D-tyrosyl-tRNA$^{Tyr}$ editing activity was observed for any of the single or multiple TyrRS-FRSed mutants. Based on these data, the inventors concluded that introducing activating mutations into the phenylalanyl-tRNA synthetase editing domain only affects its activity towards L-tyrosyl-tRNA$^{Tyr}$ and does not alter its stereo-specificity.

Free Energy Analysis of Editing Domain Variants.

To quantify the effect that each of the editing domain variants had on the L-tyrosyl-tRNA$^{Tyr}$ hydrolysis reaction, the $K_m^{L\text{-}Tyr\text{-}tRNA}$ and $k_{cat}$ values were used to calculate relative standard free energy values for the TyrRS-FRSed•L-Tyr-tRNA and TyrRS•[L-Tyr-tRNA]‡ complexes (where "‡" indicates the transition state). These values are shown, along with the relative standard free energy for activation in Table 3. Of the single variants, F145A and S211A had the largest effect on the relative standard free energy value for the TyrRS•L-Tyr-tRNA complex ($\Delta G°_{TyrRS•Tyr\text{-}tRNA}$), increasing the stability of this complex by 3.5 and 4.0 kJ/mol, relative to that of the wild-type TyrRS-FRSed, respectively. The F145A and L202A variants had the largest effect on the activation energies, decreasing the activation energies of these variants by 3.7 and 4.0 kJ/mol, respectively. The variants that had the largest effect on the free energy of the transition state complex ($\Delta G°_{TyrRS•[Tyr\text{-}tRNA]‡}$) were F145A and S211A (7.2 and 6.6 kJ/mol, respectively), with stabilization coming from both increased binding ($K_m$) and decreased activation energy ($k_{cat}$) for the F145A variant, while binding effects dominated in stabilizing the transition state complex for the S211A variant.

Figure 5:
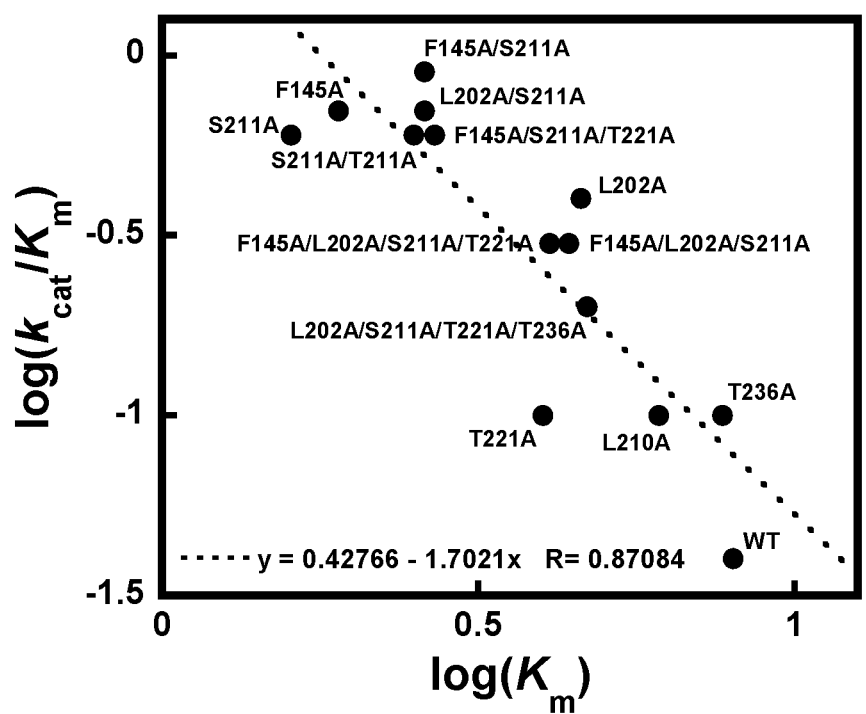
FIG. 5 shows a linear free energy relationship between K$_m$ and k$_{cat}$/K$_m$ values that is consistent with an early transition state for the hydrolysis of L-Tyr-tRNA. A linear free energy plot is shown for the TyrRS-FRSed editing domain variants investigated in this study. Log(K$_m$) and log(k$_{cat}$/K$_m$) are proportional to the stabilities of the Michaelis complex (TyrRS•Tyr-tRNA$^{Tyr}$) and transition state (TyrRS•[Tyr-tRNA$^{Tyr}$]$^‡$), respectively. As the data points for the F145A/S211A/T221A and L202A/S211A/T221A variants are identical, only the former is labeled on the graph (although both data points are included in the linear fit of the data).

In general, the relative standard free energies of the TyrRS•L-Tyr-tRNA and TyrRS•[L-Tyr-tRNA]‡ complexes of the multiple alanine variants were more stable and had lower activation energies than the single variants. This was seen most clearly with the double variants, which stabilized the TyrRS•L-Tyr-tRNA and TyrRS•[L-Tyr-tRNA]‡ complexes and lowered the activation energy to a greater extent than higher order (i.e. triple and quadruple) variants. Furthermore, the ranges of the relative free energy values for the TyrRS•L-Tyr-tRNA and TyrRS•[L-Tyr-tRNA]‡ complexes, as well as the activation energy, were significantly lower for the multiple variants than they were for the single variants, suggesting that introducing additional variants tends to dampen the effects of the single variants. For example, the range for $\Delta G°_{TyrRS•Tyr\text{-}tRNA}$ was 4.0 kJ/mol for the single variants and 1.6 kJ/mol for the multiple variants. Furthermore, the effect that each substitution had on the binding of Tyr-tRNA tended to correlate with the effect that the substitution had on the transition state (FIG. 5). Although there were exceptions (e.g. L202A, S211A) this trend generally held for both single and multiple variants, suggesting that the transition state for the editing domain may be similar to the TyrRS•L-Tyr-tRNA complex (i.e. the transition state occurs early in the reaction).

Quantifying Standard Free Energies of Interaction Between the Editing Domain Side Chains.

Standard free energies of interaction between side chains can be quantified using double mutant free energy cycles. Double mutant free energy cycles can be constructed for each step along the reaction pathway, allowing the effect that energetic coupling has on the stability of each complex to be determined. For example, the double mutant free energy cycle shown in FIG. 6, panel A can be used to quantify the effect that coupling between the activating alanine mutations at positions 145 and 211 (i.e. F145A and S211A) have on the stability of the TyrRS•L-Tyr-tRNA complex. For the F145A: S211A interaction, $\Delta^2 G°_{int}$ is positive, indicating that the interaction between the F145A and S211A activating mutations is antisynergistic and destabilizes the TyrRS•L-Tyr-tRNA complex. In other words, the combined effect of the F145A and S211A mutations is less than additive with respect to the stability of the TyrRS•L-Tyr-tRNA complex. Similarly, $\Delta^2 G°_{int}$ is positive for the TyrRS•[L-Tyr-tRNA]‡ complex and activation energy (FIG. 6, panels B and C), indicating that the interaction between the F145A and S211A activating mutations is antisynergistic (and destabilizing). As the alanine substitutions are effectively deletions of the F145 and S211 side chains, another way to interpret these results is that the interaction between the F145 and S211 side chains stabilizes the TyrRS•L-Tyr-tRNA and TyrRS•[L-Tyr-tRNA]‡ complexes and reduces the activation energy. Note, however, that it is only the interaction between these two side chains that has this effect, the overall effect of replacing F145 and S211 with alanine is to stabilize the TyrRS•L-Tyr-tRNA and TyrRS•[L-Tyr-tRNA]‡ complexes and lower the activation energy (although these effects are reduced due to the interaction between the F145 and S211 side chains). Similar results were seen for the L202A/S211A and T221A/S211A double variants (Supplemental Table S2, Supplemental Figure S5).

Figures 7A, 7B, 7C, 7D, 7E, 7F:
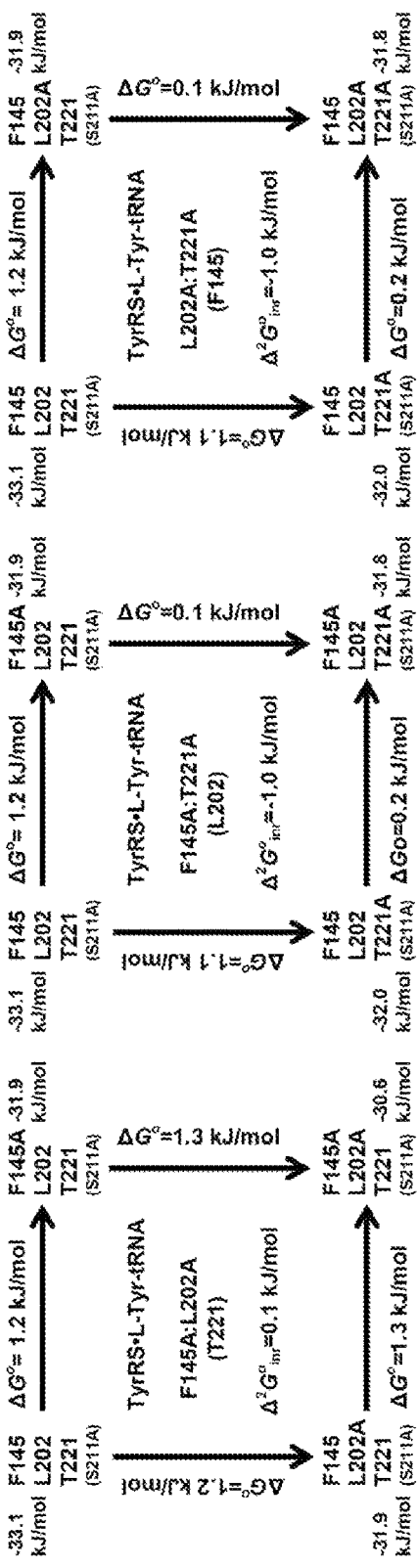
FIGS. 7A-7F show quantitation of the ternary free energy of interaction between the F145A, L202A, and T221A alanine substitutions for the TyrRS•Tyr-tRNA$^{Tyr}$ complex. The six faces of the triple mutant free energy cube are shown for the interaction between the F145A, L202A, and T221A substitutions in the TyrRS•Tyr-tRNA$^{Tyr}$ complex (FIGS. 7A-7F). Double mutant free energy cycles representing opposite faces of the cube are located in the same vertical column (e.g.

Extending the free energy of interaction analysis to higher order interactions, one can see that in the presence of S211A, the ternary interaction between the F145A, L202A, and T221A activating mutations is antisynergistic (i.e. destabilizing) for the TyrRS•L-Tyr-tRNA (compare the $\Delta^2 G°_{int}$ values in FIG. 7 panels A and D; $\Delta^3 G°_{int} = \Delta^2 G°_{int}$ (panel D)$-\Delta^2 G°_{int}$ (panel A)=0.8 kJ/mol). In contrast, this ternary interaction is synergistic for the TyrRS•[L-Tyr-tRNA]‡ complex (Supplemental Table S5, panels A and D; $\Delta^3 G°_{int}=-1.6$ kJ/mol) and the activation energy (Supplemental Table S6, panels A and D; $\Delta^3 G°_{int}=-1.7$ kJ/mol). In other words, the interaction with the third activating mutation (e.g. T221A) stabilizes the transition state and lowers the activation for the editing reaction.

Editing Domain Variants Switch the Stereospecificity of the TyrRS-FRSed Variant.

To determine the effect that increasing the activity of the editing domain had on the stereospecificity of the TyrRS-FRSed variant, four editing domain variants were selected for further analysis: wild-type TyrRS-FRSed, an editing defective variant (N217A), and two variants containing activating mutations in the editing domain (T221A and F145A/S211A). To quantify the stereospecificity of the TyrRS-FRSed editing domain, a competition assay was performed. In this assay, the TyrRS-FRSed variants were incubated in the presence of 10 mM MgATP, 10 μM tRNA$^{Tyr}$, 30 μM [$^{14}$C]L-tyrosine, and varying amounts of [$^3$H]D-tyrosine, and the formation of L- and D-tyrosyl-tRNA$^{Tyr}$ was monitored by determining the amount of [$^{14}$C]L-tyrosine and [$^3$H]D-tyrosine incorporated into the Tyr-tRNA product. This competition assay has previously been used to demonstrate that ability of D-tyrosine to compete with L-tyrosine in the aminoacylation reaction is ~2-fold higher for the TyrRS-FRSed variant than it is for the wild type tyrosyl-tRNA synthetase, as shown in the Appendix manuscript.

Figure 8:
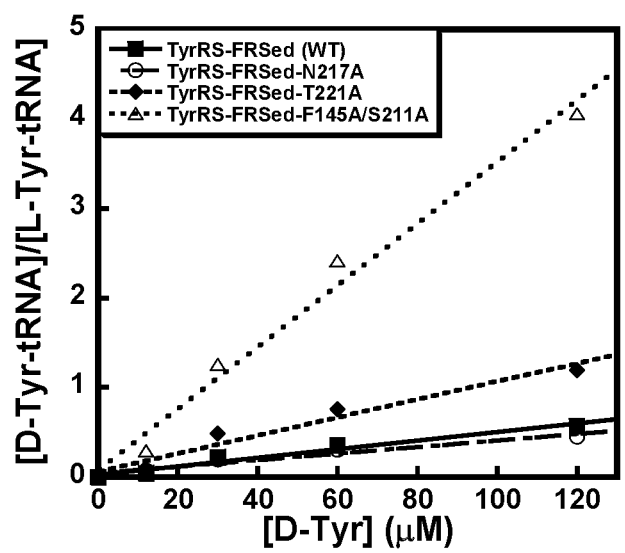
FIG. 8 shows competition between L- and D-tyrosine for aminoacylation of tRNA for selected TyrRS-FRSed variants. Competition assays were performed in the presence of 30 μM [$^{14}$C]-labeled L-tyrosine and varying concentrations of [$^3$H]-labeled D-tyrosine. The ratio of [D-Tyr-tRNA]/[L-Tyr-tRNA] produced after 15 minutes is shown the wild-type TyrRS-FRSed (squares), TyrRS-FRSed-N217A (circles), TyrRS-FRSed-T221A (diamonds), and TyrRS-FRSed-F145A/S211A (triangles) variants.
Figure 9A:
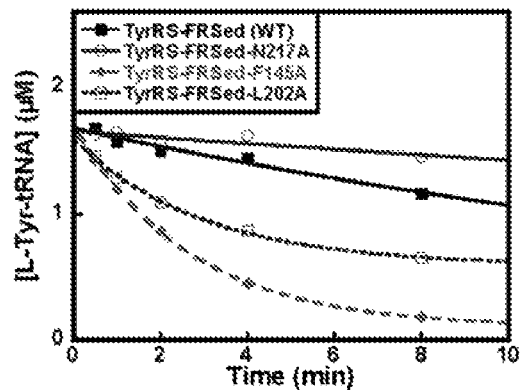
FIGS. 9A-9D show trans-editing of L-Tyr-tRNA$^{Tyr}$ by alanine variants of the TyrRS-FRSed. Representative plots for the hydrolysis of L-[$^{14}$C]Tyr-tRNA$^{Tyr}$ are shown for the TyrRS-FRSed editing domain variants.
Figure 9B:
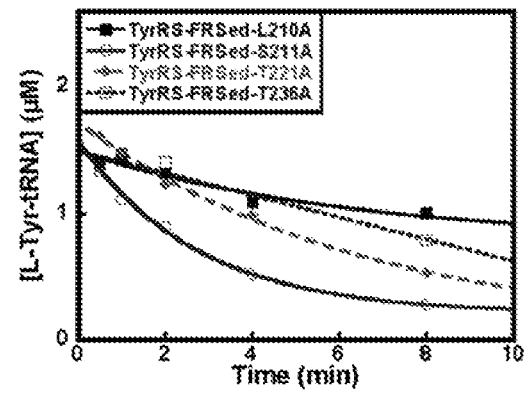
Figure 9C:
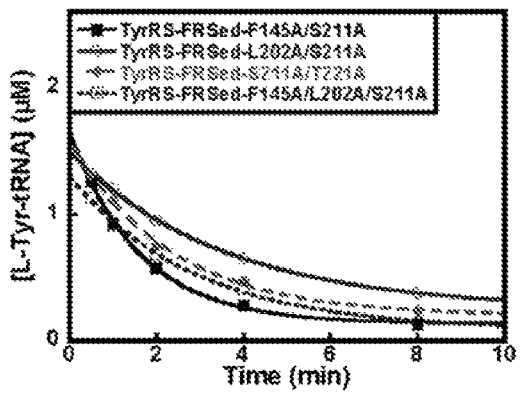
Figure 9D:
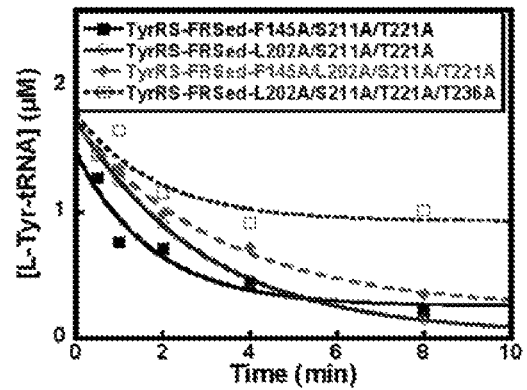
Figure 10A:
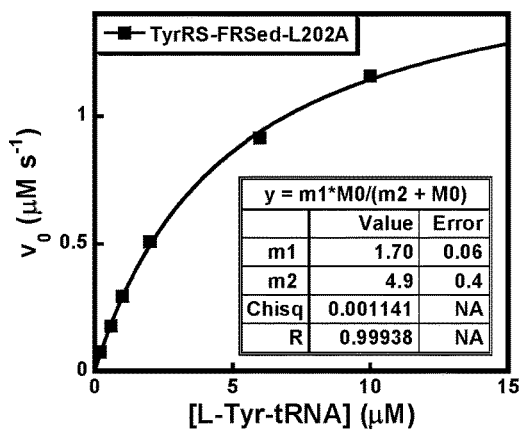
FIGS. 10A-10K show steady-state kinetic analysis of L-Tyr-tRNA$^{Tyr}$ hydrolysis by the TyrRS-FRSed variants. Representative plots of initial rate vs. substrate concentration are shown for the hydrolysis of L-Tyr-tRNA$^{Tyr}$ by the TyrRS-FRSed variants. Hydrolysis of L-tyrosyl-tRNA$^{Tyr}$ was monitored using the coupled assay shown in FIG. 3. The data are fit to the Michaelis-Menten equation (equation 2). Steady-state kinetics are shown for the TyrRS-FRSed-L202A (FIG. 10A), TyrRS-FRSed-L210A (FIG. 10B), TyrRS-FRSed-T221A (FIG. 10C), TyrRS-FRSed-T236A (FIG. 10D), TyrRS-FRSed-L202A/S211A (FIG. 10E), TyrRS-FRSed-S211A/T221A (FIG. 10F), TyrRS-FRSed-F145A/L202A/S211A (FIG. 10G), TyrRS-FRSed-F145A/S211A/T221A (FIG. 10H), TyrRS-FRSed-L202A/S211A/T221A (FIG. 10I), TyrRS-FRSed-F145A/L202A/S211A/T221A (FIG. 10J), and TyrRS-FRSed-L202A/S211A/T221A/T236A (FIG. 10K) variants.
Figure 10B:
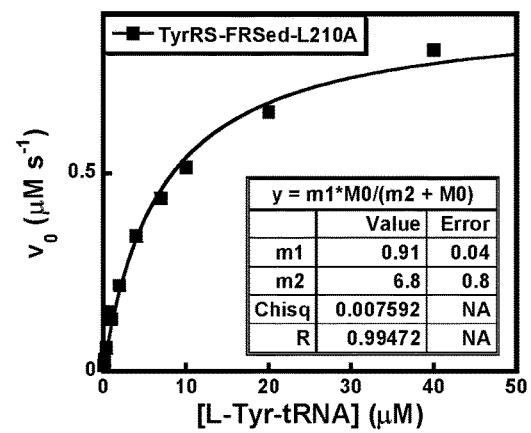
Figure 10C:
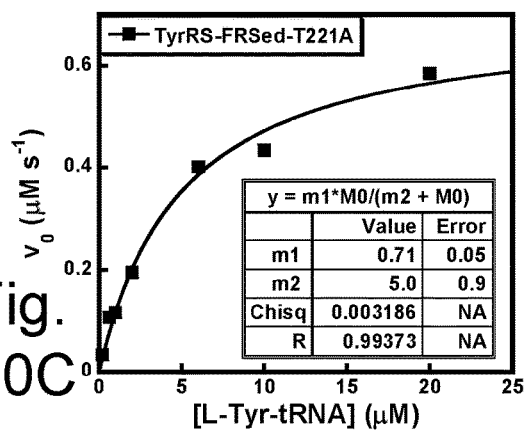
Figure 10D:
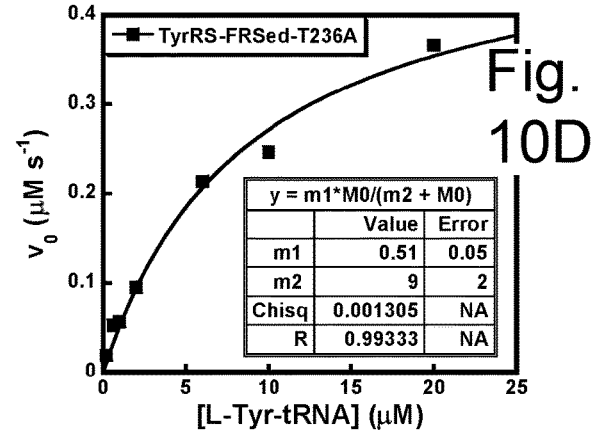
Figure 10E:
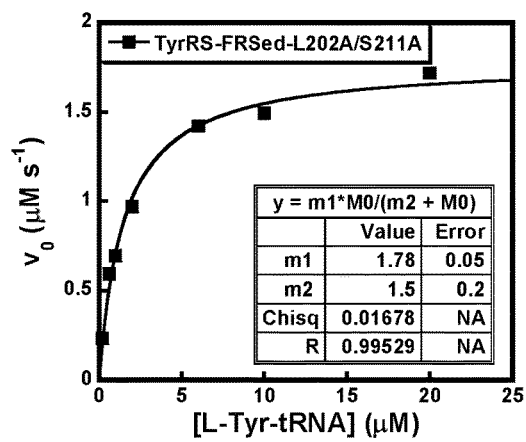
Figure 10F:
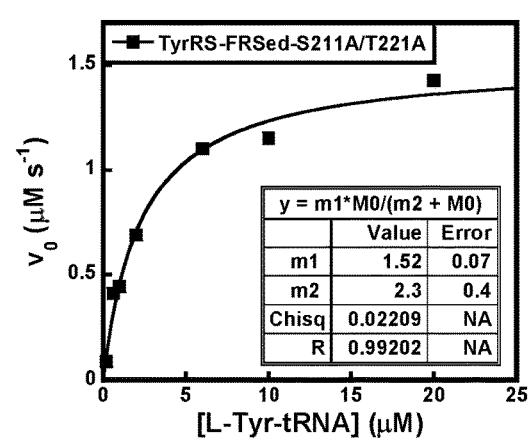
Figure 10G:
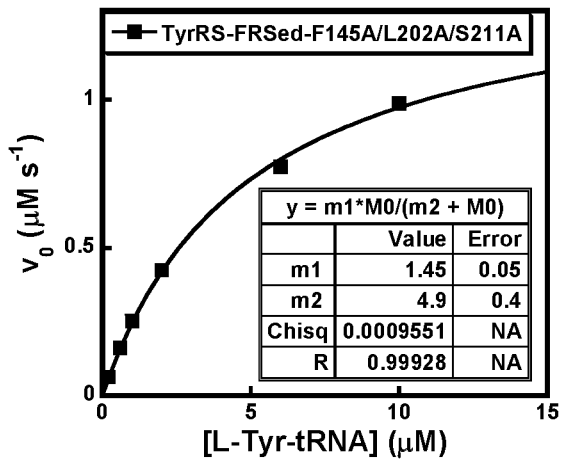
Figure 10H:
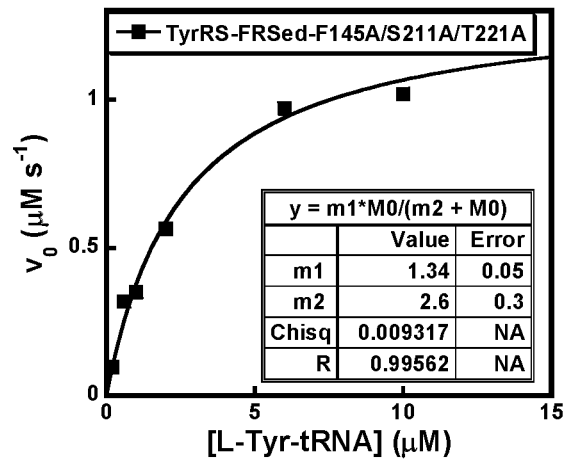
Figure 10I:
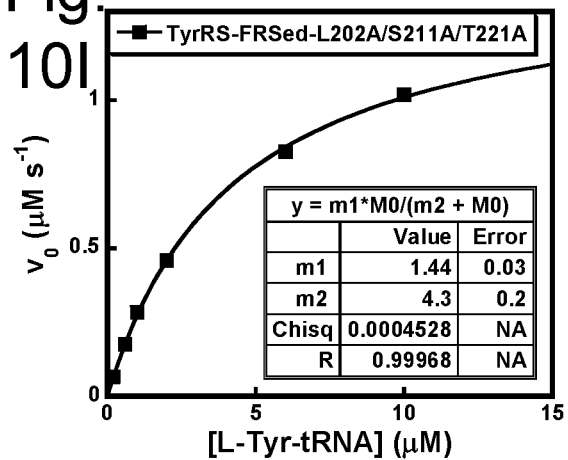
Figure 10J:
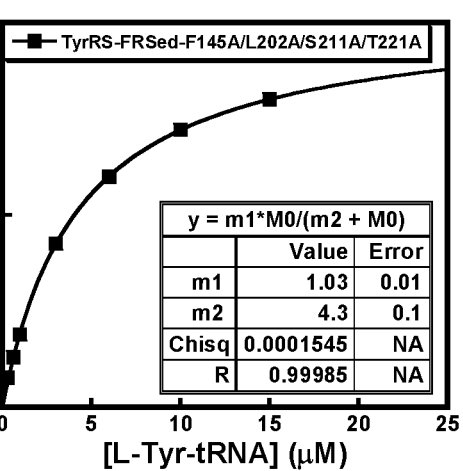
Figure 10K:
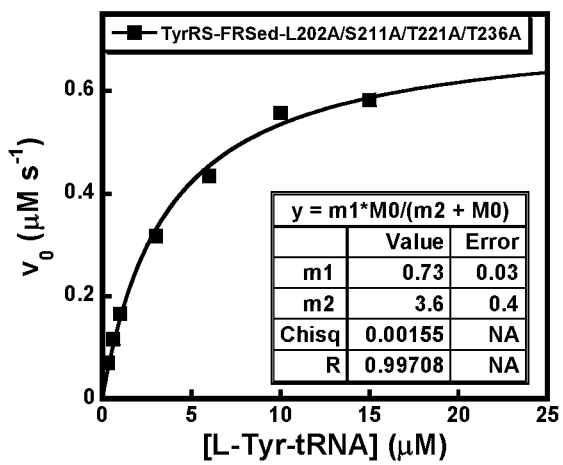

Turning to FIG. 8, at equimolar concentrations of D- and L-tyrosine (i.e. 30 μM), the ratio of D-Tyr-tRNA$^{Tyr}$ to L-Tyr-tRNA$^{Tyr}$ produced by the wild-type TyrRS-FRSed variant was ~1:5. This was 2-fold higher than the ratio of D-Tyr-tRNA$^{Tyr}$ to L-Tyr-tRNA$^{Tyr}$ produced by the TyrRS-FRSed-N217A variant, which had an inactive editing domain. In contrast, introducing the editing domains containing the T221A and F145A/S211A substitutions increased the ratio of D-Tyr-tRNA$^{Tyr}$ to L-Tyr-tRNA$^{Tyr}$ to ~0.5 and 1.3, respectively. In other words, at equimolar concentrations of D- and L-tyrosine, the TyrRS-FRSed-F145A/S211A variant preferentially aminoacylated tRNA$^{Tyr}$ with D-tyrosine in the competition assay. As the competition assay was performed during the initial linear portion of the reaction using physiological concentrations of L-tyrosine, the preference for D-tyrosine over L-tyrosine represents a true reversal of tyrosyl-tRNA synthetase stereospecificity. Increasing the concentration of D-tyrosine results in an even more dramatic shift toward D-tyrosyl-tRNA$^{Tyr}$ formation, the F145A/S211A variant exhibited a four-fold preference for aminoacylation of tRNA$^{Tyr}$ by D-tyrosine at 120 µM D-tyrosine.

DISCUSSION—The insertion of the wild type *P. horikoshii* phenylalanyl-tRNA synthetase editing domain into *G. stearothermophilus* tyrosyl-tRNA synthetase was insufficient to switch the stereospecificity of the enzyme to prefer D-tyrosine over L-tyrosine at equimolar concentrations. The insertion of this editing domain, despite being stereospecific for L-tyrosyl-tRNA$^{Tyr}$ hydrolysis, showed only modest difference in stereospecificity compared to the wild-type *G. stearothermophilus* tyrosyl-tRNA synthetase.

To improve the stereospecificity of the TyrRS-FRSed chimera, the inventors sought to increase the hydrolytic activity of the inserted phenylalanyl-tRNA synthetase using single and multiple amino acid replacements. The examined enzyme variants showed increased editing activity under steady state conditions compared to the wild-type TyrRS-FRSed chimera. These activating enzyme variants showed up to 5-fold increase in the affinity for L-tyrosyl-tRNA and up to 7.5-fold increase in the rate of hydrolysis. Replacement with other amino acids could provide an increased activity, if not understanding, at the role that these amino acid residues play in substrate recognition and hydrolytic activity. It was originally suggested these enhancing variants showed an increase in product release, but this effect alone does not agree with the observed increases in L-tyrosyl-tRNA$^{Tyr}$ affinity.

One of these double amino acid replacements, the TyrRS-FRSed-F145A/S211A, showed the largest increase in the activity of the inserted phenylalanyl-tRNA synthetase editing domain. This double variant showed a preference for D-tyrosine at equimolar concentrations of L- and D-tyrosine with a strong preference at higher concentrations of D-tyrosine.

This engineered D-tyrosine specific tyrosyl-tRNA synthetase may be used for the selection of EF-1α and ribosome variants that allow the efficient incorporation of D-amino acids into protein in archaea. Specifically, the TyrRS-FRSed variant is introduced into archaeal or eukaryotic cells along with a variant of bacterial tRNA$^{Tyr}$ in which the tyrosine anticodon is replaced by an anticodon that recognizes a stop codon in mRNA (e.g. UAG). This allows incorporation of D-tyrosine at positions in the mRNA sequence containing the stop codon. A reporter coding sequence (e.g. chloramphenicol, green fluorescence protein, or luciferase) containing an internal stop codon is used to select for EF-1α or ribosome variants that increase the efficiency of incorporating D-tyrosine into the reporter protein.

Alternatively, the phenylalanyl-tRNA synthetase editing domain variants can be inserted into an archaeal or eukaryotic tyrosyl-tRNA synthetase (e.g. *Methanococcus jannaschii* tyrosyl-tRNA synthetase) and the resulting expression plasmid can be transfected into a bacterial host cell (e.g. *Escherichia coli*) along with a variant of the archaeal or eukaryotic tRNA$^{Tyr}$ in which the tyrosine anticodon is replaced by an anticodon that recognizes a stop codon in mRNA (e.g. UAG). This allows incorporation of D-tyrosine at positions in the mRNA sequence containing the stop codon. A reporter coding sequence (e.g. chloramphenicol, green fluorescence protein, or luciferase) containing an internal stop codon is used to select for EF-Tu or ribosome variants that increase the efficiency of incorporating D-tyrosine into the reporter protein.

Such a system to site-specifically incorporate D-tyrosine, or other D-amino acids, is useful for screening new peptide therapeutics within cells. Synthesized D-amino acid containing peptides have been shown to block extracellular protease activity and protein-protein interactions by acting as a non-hydrolysable mimetic; however, internalization of these peptide therapeutics has proven challenging as normal translocation motifs are less effective when they contain a D-amino acid. Introducing the necessary machinery for the orthogonal incorporation of D-amino acids into cells with a library of small peptides allows for the discovery of stable peptides of value without exogenously adding the library of in vitro synthesized peptides.

Incorporating D-amino acids into peptides and proteins has a number of advantages. Peptides containing D-amino acids are resistant to proteolysis, making them potential inhibitors of proteases. These D-peptides can be used therapeutically (for example, in the treatment of AIDS by inhibiting HIV protease). Furthermore, since they are not processed by proteolytic enzymes, D-peptides and proteins are not efficiently recognized by the immune system. Both their resistance to proteolysis and lack of recognition by the immune system increases the physiological half-life of D-peptides and proteins, providing a therapeutic advantage over L-peptides and proteins.

In addition to being resistant to proteolysis, these D-amino acid containing peptides can occupy inverse conformational space when compared to all L-amino acid containing peptides and proteins. The site specific inclusion of a D-amino acid into a polypeptide, whether randomly generated, rationally designed, or molecularly modeled peptide, has proven very important for the stabilization of the alternate conformations and unlocks protein engineering by introducing a fundamental change in the protein backbone, unlike other unnatural amino acids.

In proteins, the amino acid glycine is often used in turns as it is able to adopt conformations that are unavailable to L-amino acids. In contrast, D-amino acids are able to replace these glycine residues, as they are able to adopt the required conformation for the turn. Replacing the glycine residues with D-amino acids reduces the conformational entropy of the turn, increasing the stability of the protein. This approach can be used to create hyperstable proteins. Such proteins have a number of industrial applications (e.g. stabilization of enzymes used in laundry detergents).

The inventors have demonstrated that editing domains can be used to alter the stereospecificity of a specific class of enzymes—namely the aminoacyl-tRNA synthetases. The same approach can be used to alter or improve the stereospecificity of any enzyme. For example, aldolases catalyze the formation of carbon-carbon bonds via the aldol reaction, providing potential tools for synthesizing structurally complex chiral molecules. This potential for use in synthetic chemistry has driven efforts to alter the stereospecificity of aldolases. In particular, the stereospecificity of tagatose 1,6-bisphosphate aldolase, which catalyzes the synthesis of tagatose 1,6-bisphosphate from dihydroxyacetone phosphate and glyceraldehyde 3-phosphate, has been altered using directed evolution methods (tagatose 1,6-bisphosphate is the stereoisomer of fructose 1,6-bisphosphate). These efforts produced a variant of tagatose 1,6-bisphosphate aldolase that has a 4:1 preference for the production of fructose 1,6-bisphosphate over of tagatose 1,6-bisphosphate (wild type of tagatose 1,6-bisphosphate aldolase has a 99:1 preference for the production of tagatose 1,6-bisphosphate). The 4:1 preference of the of tagatose 1,6-bisphosphate aldolase variant could be further enhanced by introducing an editing domain (in cis or in trans) that hydrolyzes the undesired of tagatose 1,6-bisphosphate product, either regenerating the original substrates of the reaction (i.e. dihydroxyacetone phosphate and glyceraldehyde 3-phosphate) or releasing hydrolysis products that can readily be separated from the desired product (i.e. fructose 1,6-bisphosphate). Although this specific example may not have immediate industrial applications, it demonstrates through a further embodiment the value of the approach described by the inventors for altering and/or improving the stereospecificity of an enzyme. It is understood that description of the various enzymes in general and tRNA synthetases in particular include the enzyme's variants.

Tables:

TABLE 1

Steady state kinetic analysis of editing activity[1]

| TyrRS-FRSed Variant | $K_M^{Tyr\text{-}tRNA}$ (μM) | $k_{cat}$ (s$^{-1}$) | $k_{cat}/K_M$ (s$^{-1}$ μM$^{-1}$) |
|---|---|---|---|
| WT | 8 (±1) | 0.32 (±0.03) | 0.040 (±0.006) |
| F145A | 1.9 (±0.1) | 1.4 (±0.1) | 0.74 (±0.07) |
| L202A | 4.6 (±0.8) | 1.6 (±0.4) | 0.3 (±0.1) |
| L210A | 6.1 (±0.8) | 0.73 (±0.08) | 0.12 (±0.02) |
| S211A | 1.6 (±0.3) | 0.9 (±0.2) | 0.6 (±0.2) |
| T221A | 4 (±2) | 0.6 (±0.2) | 0.2 (±0.1) |
| T236A | 7.7 (±0.8) | 0.46 (±0.05) | 0.06 (±0.01) |
| F145A/S211A | 2.6 (±0.2) | 2.4 (±0.3) | 0.9 (±0.1) |
| L202A/S211A | 2.6 (±0.2) | 1.7 (±0.2) | 0.7 (±0.2) |
| S211A/T221A | 2.5 (±0.1) | 1.5 (±0.2) | 0.6 (±0.1) |
| F145A/L202A/S211A | 4.4 (±0.8) | 1.4 (±0.4) | 0.3 (±0.1) |
| F145A/S211A/T221A | 2.7 (±0.8) | 1.6 (±0.4) | 0.6 (±0.2) |
| L202A/S211A/T221A | 2.7 (±0.7) | 1.6 (±0.1) | 0.6 (±0.2) |
| F145A/L202A/S211A/T221A | 4.1 (±0.5) | 1.15 (±0.09) | 0.28 (±0.04) |
| L202A/S211A/T221A/T236A | 4.7(±0.9) | 0.9 (±0.1) | 0.19 (±0.04) |

[1]Standard errors are shown in parentheses

TABLE 2

Comparison of [$^{14}$C]L-Tyr-tRNA$^{Tyr}$ hydrolysis results with predicted results based on the $k_{cat}$ and $K_m$ values determined by spectrophotometric editing assay

| Variant | Observed rate (s$^{-1}$) | Predicted Rate[1] |
|---|---|---|
| TyrRS-FRSed (WT) | 0.0008 (±0.0003) | 0.00069 |
| TyrRS-FRSed-T221A | 0.003 (±0.001) | 0.0034 |
| TyrRS-FRSed-F145A/S221A | 0.0099 (±0.0005) | 0.012 |

[1]The predicted rate is calculated based on the $k_{cat}$ and $K_m$ values from Table 1, assuming L-Tyr-tRNA$^{Tyr}$ and TyrRS-FRSed concentrations of 1.7 μM and 12.5 nM concentrations, respectively.
Standard error values are shown in parentheses.

TABLE 3

Relative free energies for TyrRS-FRSed variants[1]

| TyrRS-FRSed Variant | $\Delta G°_{TyrRS \cdot Tyr\text{-}tRNA}$ (kJ mol$^{-1}$) | $\Delta G°_{TyrRS \cdot [Tyr\text{-}tRNA]\ddagger}$ (kJ mol$^{-1}$) | Activation Energy (kJ mol$^{-1}$) |
|---|---|---|---|
| WT | −29.1 (±0.3) | 115.2 (±0.4) | 144.3 (±0.5) |
| F145A | −32.6 (±0.1) | 108.0 (±0.2) | 140.6 (±0.3) |
| L202A | −30.4 (±0.4) | 109.8 (±0.8) | 140.3 (±0.9) |
| L210A | −29.8 (±0.3) | 112.5 (±0.4) | 142.2 (±0.5) |
| S211A | −33.1 (±0.4) | 108.6 (±0.7) | 141.7 (±0.8) |
| T221A | −31 (±1) | 112 (±1) | 143 (±2) |
| T236A | −29.2 (±0.2) | 114.2 (±0.4) | 143.4 (±0.4) |
| F145A/S211A | −31.9 (±0.2) | 107.4 (±0.4) | 139.3 (±0.4) |
| L202A/S211A | −31.9 (±0.6) | 108.3 (±0.7) | 140.1 (±0.9) |
| S211A/T221A | −32.0 (±0.1) | 108.5 (±0.3) | 140.4 (±0.4) |
| F145A/L202A/S211A | −30.6 (±0.4) | 110.1 (±0.8) | 140.6 (±0.9) |
| F145A/S211A/T221A | −31.8 (±0.6) | 109 (±1) | 140 (±1) |
| L202A/S211A/T221A | −31.8 (±0.6) | 108.5 (±0.7) | 140.3 (±0.9) |
| F145A/L202A/S211A/T221A | −30.7 (±0.3) | 110.4 (±0.4) | 141.1 (±0.5) |
| L202A/S211A/T221A/T236A | −30.4 (±0.4) | 111.3 (±0.5) | 141.7 (±0.7) |

[1]Free energies are calculated relative to the unliganded enzyme. Standard error values are shown in parentheses.

TABLE S1

Comparison of [$^{14}$C]L-Tyr-tRNA$^{Tyr}$ hydrolysis results with predicted results based on the $k_{cat}$ and $K_m$ values determined by spectrophotometric editing assay

| Variant | Observed Rate (s$^{-1}$) | Predicted Rate (s$^{-1}$) |
|---|---|---|
| WT | 0.00073 | 0.00069 |
| N217A | N/A | N/A |
| F145A | 0.00628 | 0.00878 |
| L202A | 0.00568 | 0.00531 |
| S211A | 0.00616 | 0.00549 |
| T221A | 0.00255 | 0.00336 |
| L210A | 0.00264 | 0.0018 |
| T236A | 5.4E−05 | 0.00095 |
| F145A/S211A | 0.01042 | 0.01196 |
| L202A/S211A | 0.00471 | 0.00874 |
| S211A/T221A | 0.00715 | 0.00706 |
| F145A/L202A/S211A | 0.00585 | 0.00396 |
| F145A/S211A/T221A | 0.00956 | 0.00693 |
| L202A/S211A/T221A | 0.00565 | 0.00767 |
| F145A/L202A/S211A/T221A | 0.005 | 0.00418 |
| L202A/S211A/T221A/T236A | 0.00907 | 0.003 |

$^1$The predicted rate is calculated based on the $k_{cat}$ and $K_m$ values from Table 1, assuming L-Tyr-tRNA$^{Tyr}$ and TyrRS-FRSed concentrations of 1.7 μM and 12.5 nM concentrations, respectively. Observed rate values are taken from a single experimental replicate.

TABLE S2

Free Energies of Coupling in the E•L-Tyr-tRNA Complex

| Coupling analyzed (additional alanine substitutions shown in parentheses) | $\Delta^2G°_{int}$ (kJ/mol) | Effect of the coupling on the stability of the E•L-Tyr-tRNA Complex |
|---|---|---|
| F145A:S211A | 4.7 | Destabilizing |
| L202A:S211A | 2.5 | Destabilizing |
| S211A:T221A | 3.0 | Destabilizing |
| F145A:L202A (S211A) | 0.1 | Negligible |
| F145A:T221A (S211A) | −1.0 | Stabilizing |
| L202A:T221A (S211A) | −1.0 | Stabilizing |
| F145A:L202A (S211A/T221A) | 0.9 | Destabilizing |
| F145A:T221A (L202A/S211A) | −0.2 | Negligible |
| L202A:T221A (F145A/S211A) | −0.2 | Negligible |

TABLE S3

Free Energies of Coupling in the E•[L-Tyr-tRNA]$^{‡}$ Complex

| Coupling analyzed (additional alanine substitutions shown in parentheses) | $\Delta^2G°_{int}$ (kJ/mol) | Effect of the coupling on the stability of XE•[L-Tyr-tRNA]$^{‡}$ Complex |
|---|---|---|
| F145A:S211A | 6.0 | Destabilizing |
| L202A:S211A | 5.1 | Destabilizing |
| S211A:T221A | 3.1 | Destabilizing |
| F145A:L202A (S211A) | 3.0 | Destabilizing |
| F145A:T221A (S211A) | 1.7 | Destabilizing |
| L202A:T221A (S211A) | 0.3 | Negligible |
| F145A:L202A (S211A/T221A) | 1.4 | Destabilizing |
| F145A:T221A (L202A/S211A) | 0.1 | Negligible |
| L202A:T221A (F145A/S211A) | −1.3 | Stabilizing |

TABLE S4

Free Energies of Coupling for the Activation Energy

| Coupling analyzed (additional alanine substitutions shown in parentheses) | $\Delta^2G°_{int}$ (kJ/mol) | Effect of the coupling on the Activation Energy |
|---|---|---|
| F145A:S211A | 1.3 | Destabilizing |
| L202A:S211A | 2.4 | Destabilizing |
| S211A:T221A | 0.0 | None |
| F145A:L202A (S211A) | 2.9 | Destabilizing |
| F145A:T221A (S211A) | 2.0 | Destabilizing |
| L202A:T221A (S211A) | 1.5 | Destabilizing |
| F145A:L202A (S211A/T221A) | 1.2 | Destabilizing |
| F145A:T221A (L202A/S211A) | 0.3 | Negligible |
| L202A:T221A (F145A/S211A) | −0.2 | Negligible |

TABLE S5

Ternary Free Energies of Coupling between F145A, L202A, and T221A

| Coupling analyzed (additional alanine substitutions shown in parentheses) | $\Delta^3G°_{int}$ (kJ/mol) | |
|---|---|---|
| F145A:S211A:T221A (S211A) | 0.8 | Effect of the coupling on the stability of the E•L-Tyr-tRNA Complex<br>Destabilizing |
| F145A:S211A:T221A (S211A) | −1.6 | Effect of the coupling on the stability of the E•[L-Tyr-tRNA]$^{‡}$ Complex<br>Stabilizing |
| F145A:S211A:T221A (S211A) | −1.7 | Effect of the coupling on the Activation Energy<br>Stabilizing |

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

Wherefore we claim:

1. A method for increasing D-stereospecificity of an enzyme comprising:
   introducing a stereospecific editing domain into the enzyme;
   wherein the enzyme is *Geobacillus stearothermophilus* tyrosyl-tRNA synthetase; and
   the stereospecific editing domain is amino acids 83-275 of a *Pyrococcus horikoshii* phenylalanine-tRNA synthetase β-subunit of Seq. ID. No. 1, that includes one of,
   L202A,
   L210A,
   T221A,
   T236A,
   F125A/S211A,
   L202A/S211A,
   T221A/S211A,
   F125A/S202A/S211A,
   F125A/T221A/S211A,
   L202A/T221A/S211A,
   F145A/L202A/T221A/S211A, and
   L202A/T221A/S211A/T236A
   mutations, the mutations being between one and four variants; and
   the steriospecific editing domain being inserted between G161 and I162 on the *Geobacillus stearothermophilus* tyrosyl-tRNA synthetase of Seq. ID. No. 2.

2. The method of claim 1 wherein the stereospecific editing domain includes one of,
   L202A,
   L210A,
   T221A,
   T236A,
   F125A/S211A,
   L202A/S211A,
   T221A/S211A,
   F125A/S202A/S211A,
   F125A/T221A/S211A, and
   L202A/T221A/S211A.

3. The method of claim 1 wherein the steriospecific editing domain includes one of F125A/S202A/S211A, F125A/T211A/S211A, and L202A/T211A/S211A.

4. The method of claim 3 wherein the steriospecific editing domain includes F125A/T221A/S211A.

5. The method of claim 1 wherein the stereospecific editing domain has exactly two variants and includes one of F125A/S211A, L202A/S211A, and T221A/S211A.

6. The method of claim 5 wherein the stereospecific editing domain includes F125A/S211A.

7. The method of claim 1 wherein the stereospecific editing domain includes one of F125A/T221A/S211A and F145A/L202A/T221A/S211A.

8. The method of claim 1 wherein the stereospecific editing domain includes one of T221A/S211A, F125A/T211A/S211A, and L202A/T221A/S211A.

9. The method of claim 1 wherein the enzyme causes at least one D-amino acid being used in place of a glycine residue in a translation process.

10. The method of claim 1 wherein the enzyme causes at least one D-amino acid to occupy an inverse conformational space in a translation process.

11. The method of claim 1 wherein the editing domain contains one of
    F125A/S211A,
    L202A/S211A, T221A/S211A,
F125A/S202A/S211A,
F125A/T221A/S211A, and
L202A/T221A/S211A.

12. The method of claim 11 wherein the mutations are one of
F125A/S211A,
L202A/S211A,
T221A/S211A,
F125A/S202A/S211A,
F125A/T221A/S211A, and.

13. A method for increasing D—stereospecificity of an enzyme comprising:
   introducing a stereospecific editing domain into the enzyme between adjacent glycine and isoleucine amino acids;
wherein
   the enzyme is *Geobacillus stearothermophilus* tyrosyl-tRNA synthetase;
   the steriospecific editing domain is amino acids 83-275 of a *Pyrococcus horikoshii* phenylalanyl—tRNA synthetase β-subunit of Seq. ID. No. 1, having the substitutions F125A and S211A;
   the steriospecific editing domain being inserted between G161 and I162 on the *Geobacillus stearothermophilus* tyrosyl-tRNA synthetase of Seq. ID. No. 2;
   the enzyme causes at least one D-amino acid being used in place of a glycine residue in a translation process;
   the enzyme causes at least one D-amino acid to occupy an inverse conformational space in a translation process.

* * * * *